(12) United States Patent
Forgacs et al.

(10) Patent No.: US 11,707,077 B2
(45) Date of Patent: Jul. 25, 2023

(54) ENGINEERED COMESTIBLE MEAT

(71) Applicant: The Curators of the University of Missouri, Columbia, MO (US)

(72) Inventors: Gabor Forgacs, Potsdam, NY (US); Francoise Marga, Columbia, MO (US); Karoly Robert Jakab, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 657 days.

(21) Appl. No.: 14/092,801

(22) Filed: Nov. 27, 2013

(65) Prior Publication Data

US 2014/0093618 A1 Apr. 3, 2014

Related U.S. Application Data

(62) Division of application No. 13/558,928, filed on Jul. 26, 2012, now Pat. No. 8,703,216.

(Continued)

(51) Int. Cl.
*A23L 13/00* (2016.01)
*C12N 5/00* (2006.01)
(Continued)

(52) U.S. Cl.
CPC .............. *A23L 13/00* (2016.08); *A23L 13/03* (2016.08); *C12N 5/0062* (2013.01);
(Continued)

(58) Field of Classification Search
CPC ......... A23L 1/31; A23L 13/03; C12N 5/0062; C12N 5/0697; C12N 21/08; C12N 2502/1347
(Continued)

(56) References Cited

U.S. PATENT DOCUMENTS 4,247,279 A 1/1981 Masters
4,291,992 A 9/1981 Barr et al.
(Continued)

FOREIGN PATENT DOCUMENTS

CA 2 306 346 A1 1/1999
EP 1 589 098 A1 10/2005
(Continued)

OTHER PUBLICATIONS

Notification of and Transmittal of the extended European Search Report and the written European Search Opinion, dated Apr. 7, 2015.
(Continued)

*Primary Examiner* — Nikki H. Dees
*Assistant Examiner* — Assaf Zilbering
(74) *Attorney, Agent, or Firm* — Stinson LLP

(57) ABSTRACT

Provided are engineered meat products formed as a plurality of at least partially fused layers, wherein each layer comprises at least partially fused multicellular bodies comprising non-human myocytes and wherein the engineered meat is comestible. Also provided are multicellular bodies comprising a plurality of non-human myocytes that are adhered and/or cohered to one another; wherein the multicellular bodies are arranged adjacently on a nutrient-permeable support substrate and maintained in culture to allow the multicellular bodies to at least partially fuse to form a substantially planar layer for use in formation of engineered meat. Further described herein are methods of forming engineered meat utilizing said layers.

11 Claims, 8 Drawing Sheets

Related U.S. Application Data

(60) Provisional application No. 61/511,948, filed on Jul. 26, 2011.

(51) Int. Cl.
  *C12N 5/071* (2010.01)
  *C12M 3/00* (2006.01)

(52) U.S. Cl.
  CPC .......... *C12N 5/0697* (2013.01); *C12M 21/08* (2013.01); *C12N 2502/1347* (2013.01); *C12N 2502/28* (2013.01); *C12N 2506/1307* (2013.01); *C12N 2533/76* (2013.01)

(58) Field of Classification Search
  USPC .............................. 426/92, 2, 237, 524, 665
  See application file for complete search history.

(56) References Cited

U.S. PATENT DOCUMENTS

| | | |
|---|---|---|
| 4,585,139 A | 4/1986 | Bronson et al. |
| 4,594,597 A | 6/1986 | Liu et al. |
| 4,646,106 A | 2/1987 | Howkins |
| 4,665,492 A | 5/1987 | Masters |
| 4,673,304 A | 6/1987 | Liu et al. |
| 4,772,141 A | 9/1988 | Sanders, Jr. et al. |
| 4,889,438 A | 12/1989 | Forsyth et al. |
| 4,896,980 A | 1/1990 | Sanders, Jr. et al. |
| 4,921,365 A | 5/1990 | Sanders, Jr. et al. |
| 4,948,280 A | 8/1990 | Sanders, Jr. et al. |
| 4,969,758 A | 11/1990 | Sanders, Jr. et al. |
| 4,980,112 A | 12/1990 | Masters |
| 5,016,121 A | 5/1991 | Peddle et al. |
| 5,039,297 A | 8/1991 | Masters |
| 5,040,911 A | 8/1991 | Sanders, Jr. et al. |
| 5,075,805 A | 12/1991 | Peddle et al. |
| 5,134,569 A | 7/1992 | Masters |
| 5,204,055 A | 4/1993 | Sachs et al. |
| 5,216,616 A | 6/1993 | Masters |
| 5,490,962 A | 2/1996 | Cima et al. |
| 5,492,937 A | 2/1996 | Bogentoft et al. |
| 5,546,313 A | 8/1996 | Masters |
| 5,599,695 A | 2/1997 | Pease et al. |
| 5,605,662 A | 2/1997 | Heller et al. |
| 5,658,802 A | 8/1997 | Hayes et al. |
| 5,694,324 A | 12/1997 | Masters et al. |
| 5,702,717 A | 12/1997 | Cha et al. |
| 5,739,832 A | 4/1998 | Heinzl et al. |
| 5,797,898 A | 8/1998 | Santini, Jr. et al. |
| 5,798,779 A | 8/1998 | Nakayasu et al. |
| 5,831,070 A | 11/1998 | Pease et al. |
| 5,929,208 A | 7/1999 | Heller et al. |
| 6,087,102 A | 7/2000 | Chenchik et al. |
| 6,103,528 A | 8/2000 | An et al. |
| 6,109,717 A | 8/2000 | Kane et al. |
| 6,123,861 A | 9/2000 | Santini, Jr. et al. |
| 6,132,468 A | 10/2000 | Mansmann |
| 6,139,831 A | 10/2000 | Shivashankar et al. |
| 6,171,797 B1 | 1/2001 | Perbost |
| 6,197,575 B1 | 3/2001 | Griffith et al. |
| 6,239,273 B1 | 5/2001 | Pease et al. |
| 6,261,493 B1 | 7/2001 | Gaylo et al. |
| 6,336,480 B2 | 1/2002 | Gaylo et al. |
| 6,341,952 B2 | 1/2002 | Gaylo et al. |
| 6,387,707 B1 | 5/2002 | Seul et al. |
| 6,394,585 B1 | 5/2002 | Ross |
| 6,402,403 B1 | 6/2002 | Speakman |
| 6,419,883 B1 | 7/2002 | Blanchard |
| 6,451,346 B1 | 9/2002 | Shah et al. |
| 6,454,811 B1 | 9/2002 | Sherwood et al. |
| 6,455,311 B1 | 9/2002 | Vacanti |
| 6,495,102 B1 | 12/2002 | Suslick et al. |
| 6,497,510 B1 | 12/2002 | Delametter et al. |
| 6,514,518 B2 | 2/2003 | Monkhouse et al. |
| 6,527,378 B2 | 3/2003 | Rausch et al. |
| 6,536,873 B1 | 3/2003 | Lee et al. |
| 6,536,895 B2 | 3/2003 | Kashiwagi et al. |
| 6,538,089 B1 | 3/2003 | Samra et al. |
| 6,543,872 B2 | 4/2003 | Ohtsuka et al. |
| 6,547,994 B1 | 4/2003 | Monkhouse et al. |
| 6,548,263 B1 | 4/2003 | Kapur et al. |
| 6,550,904 B2 | 4/2003 | Koitabashi et al. |
| 6,561,626 B1 | 5/2003 | Min et al. |
| 6,561,642 B2 | 5/2003 | Gonzalez |
| 6,565,176 B2 | 5/2003 | Anderson et al. |
| 6,835,390 B1 * | 12/2004 | Vein ..................... C12N 5/0062 424/439 |
| 6,942,830 B2 | 9/2005 | Mulhaupt et al. |
| 6,979,670 B1 | 12/2005 | Lyngstadaas et al. |
| 7,051,654 B2 | 5/2006 | Boland et al. |
| 7,270,829 B2 | 9/2007 | Van Eelen |
| 7,625,198 B2 | 12/2009 | Lipson et al. |
| 8,143,055 B2 | 3/2012 | Forgacs et al. |
| 8,241,905 B2 | 8/2012 | Forgacs et al. |
| 8,728,807 B2 | 5/2014 | Forgacs et al. |
| 8,852,932 B2 | 10/2014 | Forgacs et al. |
| 9,556,415 B2 | 1/2017 | Forgacs et al. |
| 9,752,116 B2 | 9/2017 | Forgacs et al. |
| 2002/0031500 A1 | 3/2002 | MacLaughlin et al. |
| 2002/0059049 A1 | 5/2002 | Bradbury et al. |
| 2002/0064808 A1 | 5/2002 | Mutz et al. |
| 2002/0064809 A1 | 5/2002 | Mutz et al. |
| 2002/0084290 A1 | 7/2002 | Materna |
| 2002/0089561 A1 | 7/2002 | Weitzel et al. |
| 2002/0090720 A1 | 7/2002 | Mutz et al. |
| 2002/0106412 A1 | 8/2002 | Rowe et al. |
| 2002/0160109 A1 | 10/2002 | Yeo et al. |
| 2002/0173586 A1 | 11/2002 | Jeong et al. |
| 2002/0182633 A1 | 12/2002 | Chen et al. |
| 2002/0188349 A1 | 12/2002 | McAllister et al. |
| 2003/0003575 A1 | 1/2003 | Vacanti et al. |
| 2003/0032203 A1 | 2/2003 | Sabatini et al. |
| 2003/0059537 A1 | 3/2003 | Chilkoti et al. |
| 2003/0100824 A1 | 5/2003 | Warren et al. |
| 2003/0153078 A1 | 8/2003 | Libera et al. |
| 2003/0175410 A1 | 9/2003 | Campbell et al. |
| 2004/0219133 A1 | 11/2004 | Lyles |
| 2004/0237822 A1 | 12/2004 | Boland et al. |
| 2004/0253365 A1 | 12/2004 | Warren et al. |
| 2005/0084958 A1 | 4/2005 | Vein |
| 2005/0276791 A1 | 12/2005 | Hansford et al. |
| 2006/0029922 A1 * | 2/2006 | Van Eelen ........... C12N 5/0658 435/1.1 |
| 2006/0121006 A1 * | 6/2006 | Chancellor .......... C12N 5/0652 424/93.7 |
| 2007/0142916 A1 | 6/2007 | Olson, Jr. et al. |
| 2007/0231787 A1 | 10/2007 | Voelker |
| 2008/0070304 A1 | 3/2008 | Forgacs et al. |
| 2009/0142307 A1 | 6/2009 | Athanasiou et al. |
| 2009/0208466 A1 | 8/2009 | Yoo et al. |
| 2009/0248145 A1 | 10/2009 | Chan et al. |
| 2010/0041134 A1 * | 2/2010 | Forgacs ................ A61L 27/222 435/325 |
| 2011/0212501 A1 | 9/2011 | Yoo |
| 2012/0023777 A1 | 2/2012 | Greene |
| 2014/0220685 A1 | 8/2014 | Forgacs et al. |
| 2015/0004273 A1 | 1/2015 | Forgacs et al. |
| 2015/0344828 A1 | 12/2015 | Forgacs et al. |
| 2016/0130551 A1 | 5/2016 | Forgacs et al. |
| 2016/0348067 A1 | 12/2016 | Forgacs et al. |
| 2017/0145386 A1 | 5/2017 | Forgacs et al. |
| 2017/0152474 A1 | 6/2017 | Forgacs et al. |

FOREIGN PATENT DOCUMENTS

| | | |
|---|---|---|
| EP | 2 090 584 A1 | 8/2009 |
| WO | 99/31222 A1 | 6/1999 |
| WO | 01/68811 A2 | 9/2001 |
| WO | 2005/081970 A2 | 9/2005 |
| WO | 2007/124023 A2 | 11/2007 |

(56) References Cited

FOREIGN PATENT DOCUMENTS

| WO | 2010/008905 A2 | 1/2010 |
|---|---|---|
| WO | 2012/054195 A2 | 4/2012 |

OTHER PUBLICATIONS

Hopkins, P.D. and Dacey, A. Vegetarian Meat: Could Technology Save Animals and Satisfy Meat Eaters? J Agric Environ Ethics (published online Jul. 11, 2008) pp. 579-596, vol. 21, Springer Science.

Yang, J. et al. Cell sheet engineering: Recreating tissues without biodegradable scaffolds. (published online Jul. 11, 2005) Biomaterials, pp. 6415-6422, vol. 26, Elsevier.

Sekine, H., et al., Myocardial tissue reconstruction: The cell sheet engineering approach, (published May 2007) Inflammation and Regeneration, pp. 171-176, vol. 27 No.3.

Matsuda, N., et al., Tissue Engineering Based on Cell Sheet Technology, (published 2007) Adv. Materials, pp. 3089-3099, vol. 19, WILEY-VCH Verlag GmbH & Co. KGaA, Weinheim.

Aldhous, P. Print me a heart and a set of arteries. (published Apr. 15, 2006) New Scientist., Issue 2547, p. 19.

Barnard, N. D., et al., "The Medical Costs Attributable to Meat Consumption," Preventative Medicine, 1995, pp. 646-655, vol. 24, No. 6.

Benjaminson, M. A., et al. "In vitro Edible Muscle Protein Production System (MPPS): Stage 1, fish.," Acta Astronautica, 2002, pp. 879-889, vol. 51, No. 12.

Bhat, Z. F., et al., "Animal-free Meat Biofabrication," American Journal of Food Technology, 2011, pp. 441-459, vol. 6, No. 6.

Bhat, Z. F., et al., "Tissue Engineered Meat-Future Meat," Journal of Stored Products and Postharvest Research, 2011, pp. 1-10, vol. 2, No. 1.

Boonen, K. J., et al., "Essential Environmental Cues from the Satellite Cell Niche: Optimizing Proliferation and Differentiation," American Journal of Physiology. Cell Physiology, 2009, pp. C1338-C1345, vol. 296, No. 6.

Boonen, K. J., et al., "The Muscle Stem Cell Niche: Regulation of Satellite Cells During Regeneration," Tissue Engineering, Part B, Reviews, 2008, pp. 419-431, vol. 14, No. 4.

Datar, I., et al., "Possibilities for an In Vitro Meat Production System," Innovative Food Science & Emerging Technologies, 2010, pp. 13-22, vol. 11, Issue 1.

De Deyne, P.G., "Formation of Sarcomeres in Developing Myotubes: Role of Mechanical Stretch and Contractile Activation," American Journal of Physiology. Cell Physiology, 2000, pp. C1801-C1811, vol. 279, No. 6.

Dennis, R. G., et al., "Excitability and Isometric Contractile Properties of Mammalian Skeletal Muscle Contructs Engineered In Vitro," In Vitro Cellular & Developmental Biology Animal, 2000, pp. 327-335, vol. 36, No. 5.

Dennis, R. G., et al., "Excitability and contractility of skeletal muscle engineered from primary cultures and cell lines," In Vitro Cellular & Developmental Biology. Animal, 2001, pp. C288-C295, vol. 280, No. 2.

Edelman, E. R., "Vascular Tissue Engineering: Designer Arteries," Circulation Research, 1999, pp. 1115-1117, vol. 85, No. 12.

Edelman, P. D., et al., "Commentary: In Vitro-cultured Meat Production," Tissue Engineering, 2005, pp. 659-662, vol. 11, Nos. 5-6.

Engler, A. J., et al., "Myotubes Differentiate Optimally on Substrates with Tissue-like Stiffness: Pathological Implications for Soft or Stiff Microenvironments," The Journal of Cell Biology, 2004, pp. 877-887, vol. 166, No. 6.

European Food Safety Authority, "The Community Summary Report on Trends and Sources of Zoonoses, Zoonotic Agents, Antimicrobial Resistance and Foodborne Outbreaks in the European Union in 2005," EFSA Journal, 2006, pp. 2-288, vol. 94r.

Fonseca, S., et al., "Slow Fiber Cluster Pattern in Pig Longissimus Thoracis Muscle: Implications for Myogenesis," Journal of Animal Science, 2003, pp. 973-983, vol. 81, No. 4.

Gawlitta I A, D., et al., "The Influence of Serum-free Culture Conditions on Skeletal Muscle Differentiation in a Tissue-engineered Model," Tissue Engineering, Part A, 2008, pp. 161-171, vol. 14, No. 1.

Jakab, K., et al., "Engineering Biological Structures of Prescribed Shape Using Self-assembling Multicellular Systems," Proceedings of the National Academy of Sciences of the United States of America, 2004, pp. 2864-2869, vol. 101, No. 9.

Katsumata, M., et al., "Promotion of Intramuscular Fat Accumulation in Porcine Muscle by Nutritional Regulation," Animal Science Journal, 2011, pp. 17-25, vol. 82, No. 1.

Kosnik, P. E., et al., "Tissue Engineering Skeletal Muscle," Functional Tissue Engineering, 2003, pp. 377-392, Springer, New York, New York.

Langelaan, M. L. P., et al., "Meet the New Meat: Tissue Engineered Skeletal Muscle," Trends in Food Science & Technology, 2010, pp. 59-66, vol. 21, No. 2.

Lee, W., et al., "Multi-layered Culture of Human Skin Fibroblasts and Keratinocytes Through Three-dimensional Freeform Fabrication," Biomaterials, 2009, pp. 1587-1595, vol. 30, No. 8.

Levenberg, S., et al., "Engineering Vascularized Skeletal Muscle Tissue," Nature Biotechnology, 2005, pp. 879-884, vol. 23, No. 7.

Marga, F., et al., "Toward Engineering Functional Organ Modules by Additive Manufacturing," Biofabrication, 2012, 12 pages, vol. 4, No. 2.

Mead, P. S., et al., "Food-related Illness and Death in the United States," Emerging Infectious Diseases, 1999, pp. 607-625, vol. 5, No. 5.

Mironov, V., et al., "Bioprinting Living Structures," Journal of Materials Chemistry, 2007, pp. 2054-2060, vol. 17, No. 20.

Niklason, L. E., et al., "Advances in Tissue Engineering of Blood Vessels and Other Tissues," Transplant Immunology, 1997, pp. 303-306, vol. 5, No. 4.

Norotte, C., et al., "Scaffold-free Vascular Tissue Engineering Using Bioprinting," Biomaterials, 2009, pp. 5910-5917, vol. 30, No. 30.

Park, H., et al., "Effects of electrical stimulation in C2C12 muscle constructs," Journal of Tissue Engineering and Regenerative Medicine, 2008, pp. 279-287, vol. 2, No. 5.

Perez-Pomares, J. M., et al., "Tissue Fusion and Cell Sorting in Embryonic Development and Disease: Biomedical Implications," BioEssays, 2006, pp. 809-821, vol. 28, No. 8.

Pette, D., et al., "What does chronic electrical stimulation teach us about muscle plasticity?," Muscle & Nerve, 1999, pp. 666-677, vol. 22, No. 6.

Savadogo, P., et al., "Effects of Grazing Intensity and Prescribed Fire on Soil Physical and Hydrological Properties and Pasture Yield in the Savanna Woodlands of Burkina Faso," Agriculture, Ecosystems & Environment, 2007, pp. 80-92, vol. 118, Nos. 1-4.

Smith, C. M., et al., "Three-dimensional Bioassembly Tool for Generating Viable Tissue-engineered Constructs," Tissue Engineering, 2004, pp. 1566-1576, vol. 10, Nos. 9-10.

Thelen, M. H., et al., "Electrical Stimulation of C2C12 Myotubes Induces Contractions and Represses Thyroid-hormone-dependent Transcription of the Fast-type Sarcoplasmic-reticulum Ca2+-ATPase Gene," The Biochemical Journal, 1997, pp. 845-848, vol. 321, Part 3.

Tuomisto, H. L., et al., "Environmental Impacts of Cultured Meat Production," Environmental Science & Technology, 2011, pp. 6117-6123, vol. 45, No. 14.

PCT/US2005/05735, International Search Report dated Dec. 7, 2007.

PCT/US2011/023520 International Search Report dated Oct. 31, 2011.

PCT/US2009/048530 International Search Report dated Mar. 15, 2010.

PCT/US2011/053515 International Search Report and Written Opinion dated May 1, 2012.

PCT/US2012/048357 International Search Report dated Feb. 15, 2013.

* cited by examiner

ENGINEERED COMESTIBLE MEAT

CROSS-REFERENCE TO RELATED APPLICATIONS

This application is a divisional of U.S. patent application Ser. No. 13/558,928 filed on Jul. 26, 2012, which claims the benefit under 35 U.S.C. §119(e) of U.S. Provisional Application No. 61/511,948, filed Jul. 26, 2011, both of which are incorporated herein by reference in their entireties.

BACKGROUND OF THE INVENTION

Protein is a nutrient needed by the human body for growth and maintenance. Aside from water, protein is the most abundant molecule in the body. According to U.S. and Canadian Dietary Reference Intake guidelines, women aged 19-70 need to consume 46 grams of protein per day, while men aged 19-70 need to consume 56 grams of protein per day to avoid deficiency. This recommendation, however, is for a sedentary person free of disease. Protein deficiency can lead to reduced intelligence or mental retardation as well as contribute to the prevalence of diseases such as kwashiorkor. Protein deficiency is a serious problem in developing countries, particularly, in countries affected by war, famine, and overpopulation. Animal sources of protein, such as meat, are often a source of the complete complement of all the essential amino acids in adequate proportions.

The nutritional benefits of meat are tempered by potential associated environmental degradation. According to a 2006 report by the Livestock, Environment And Development Initiative, entitled Livestock's Long Shadow-Environmental Issues and Options, the livestock industry is one of the largest contributors to environmental degradation worldwide, and modern practices of raising animals for food contributes widely to air and water pollution, land degradation, climate change, and loss of biodiversity. The production and consumption of meat and other animal sources of protein is also associated with the clearing of rainforests and species extinction. Accordingly, there is a need for a solution to demands for alternative to meat produced from live animals.

SUMMARY OF THE INVENTION

Tissue engineering technology offers new opportunities to produce edible sources of animal protein that are not associated with the environmental degradation of raising livestock. Tissue engineering has been defined as an interdisciplinary field that applies the principles of engineering and life sciences toward the development of biological substitutes that restore, maintain, or improve tissue function or a whole organ. Langer R, Vacanti J P, *Tissue Engineering*, Science 260(5110):920-926 (May 1993). Despite the potential to apply tissue engineering technology to meet the nutritional needs of living beings, scientifically sound and industrially feasible processes have not been developed to produce comestible meat and engineered comestible meat products are not available.

Disclosed herein are engineered meat products, layers comprising a plurality of multicellular bodies for use in production of said meat, and methods of producing the engineered meat products. In a first aspect, disclosed herein is engineered meat comprising a plurality of layers, wherein each layer comprises non-human myocytes and wherein the engineered meat is comestible and for ingestion.

Also described herein are engineered meat products, the meat product comprising: a body having a volume, wherein the body comprises a plurality of stacked planar layers, wherein the layers are at least partially fused and each planar layer comprises a plurality of at least partially fused non-human multicellular bodies comprising myocytes; further wherein the body does not include any blood vessels, and wherein the engineered meat product is comestible and for ingestion.

The body volume may be greater than some minimum volume (e.g., greater than 0.1 $cm^3$, greater than 1 $cm^3$, greater than 10 $cm^3$, greater than 50 $cm^3$, greater than 100 $cm^3$, greater than 500 $cm^3$, greater than 1000 $cm^3$, etc., including any intermediate volume).

The layered nature of the engineered meat may be visible upon examination of the volume or meat. For example, the meat may have planar layers in which the myocytes are differently oriented between layers. In some variations, the layered organization of the engineered meat may be apparent by looking at regions of cell death. For example, the planar layers within a middle region of the meat product may have experienced cell death before the outer layers of the engineered meat. As described in greater detail below, formation of the engineered meat by successively stacking fused (or partially fused) planar layer atop one another and allowing the stacked layers to fuse may result in regions of cell death as successively "deeper" layers are separated further from fresh nutrients in the culture media. This may result in a pattern of cell death in which deeper regions (which may be stratified into planar layers) further from the edges of the volume experience cell death before more newly applied layers. The stratified pattern of timing of cell death may be visualized by examining markers for cell death progression, including nuclear fragmentation, and other metabolic markers, known in the art. For example, Terminal deoxynucleotidyl transferase dUTP nick end labeling (TUNEL) may be used. The planar layers may be formed of multicellular bodies having additional non-human cell types. For example, each planar layer of the engineered meat volume may comprise a plurality of at least partially fused multicellular bodies comprising non-human myocytes and one or more of: non-human endothelial cells, non-human fibroblasts, and/or non-human adipose cellsor the like.

In general, the engineered meat does not include any filler bodies, such as may be found in other forms of engineered tissues. For example, filler bodies that act as scaffolding (e.g., support structures) are not necessary, and may be detrimental to the final comestible product. Filler bodies may include biocompatible material that resists migration and ingrowth of cells from the multicellular bodies and that is resistant to adherence of cells to it. See, e.g., U.S. Pat. No. 8,143,055, herein incorporated by reference in its entirety.

The term "comestible," as used herein, means edible or suitable to be eaten by a human being or a non-human animal. The phrase "for ingestion," as used herein, means suitable and adapted to be consumed orally by a human being or a non-human animal. In some embodiments, each layer of the engineered meat further comprises non-human endothelial cells. In some embodiments, each layer of the engineered meat further comprises non-human adipose cells. In some embodiments, each layer further comprises non-human fibroblast cells. In some embodiments, the engineered meat disclosed herein comprises a plurality of layers, wherein each layer comprises non-human myocytes and wherein each layer is characterized by a thickness adapted to allow diffusion to sufficiently support the maintenance and growth of the non-human myocytes in culture. In various embodiments, the engineered meat comprises a plurality of layers, wherein each layer is about 100, 200, 300, 400, 500, 600, 700, 800, 900, or 1000 µm thick. The term "about," as used herein when referring to a measurable value, and may mean within +/−2%, +/−5%, or +/−10% of a given value or range. In some embodiments, the thickness of each layer is about 100 µm to about 1000 µm. In further embodiments, the thickness of each layer is about 150 µm to about 900 µm. In still further embodiments, the thickness of each layer is about 200 µm to about 800 µm. In still further embodiments, the thickness of each layer is about 250 µm to about 700 µm. In still further embodiments, the thickness of each layer is about 300 µm to about 600 µm. In various embodiments, the engineered meat comprises 2, 3, 4, 5, 6, 7, 8, 9, or 10 layers. In other various embodiments, the engineered meat comprises 10, 20, 30, 40, 50, 60, 70, 80, 90, or 100 layers. In some embodiments, the engineered meat disclosed herein comprises about 2 to about 100 layers. In further embodiments, the engineered meat comprises about 20 to about 80 layers. In still further embodiments, the engineered meat comprises about 40 to about 60 layers. In some embodiments, each layer comprises multicellular bodies of about 100, 200, 300, 400, 500 µm in diameter. In some embodiments, the diameter of said multicellular bodies is about 100 µm to about 500 µm. In further embodiments, the diameter of said multicellular bodies is about 200 µm to about 400 µm. In further embodiments, the diameter of said multicellular bodies is about 200 µm to about 300 µm. In still further embodiments, the diameter of said multicellular bodies is about 250 µm to about 400 µm. In still further embodiments, the diameter of said multicellular bodies is about 300 µm to about 400 µm. In general, the diameter of a multicellular body may refers to the length of the longest line extending through the midpoint a cross-section through the elongate multicellular body from one side of the sectioned multicellular body to the opposite side.

In some embodiments, the engineered meat disclosed herein is characterized by a composition that is substantially 60-80 percent aqueous fluid, 14-35 percent protein, 1-25 percent fat, 1-5 percent carbohydrates and 1-5 percent other substances. In further embodiments, the engineered meat has substantially the same composition with respect to percent proteins, fat, carbohydrates and the like as beef, veal, pork, chicken, or fish. In some embodiments, the engineered meat comprises a plurality of layers, wherein each layer comprises non-human myocytes and non-human endothelial cells and wherein each layer is bioprinted. In various embodiments, the engineered meat disclosed herein comprises a plurality of layers, wherein each layer comprises myocytes, and may include one or more of endothelial cells, adipose cells, and/or fibroblasts, wherein the cells are derived from sources including, but not limited to, mammals, birds, reptiles, fish, crustaceans, mollusks, and cephalopods, or combinations thereof. In some embodiments, the engineered meat comprises non-human myocytes, which are skeletal myocytes. In some embodiments, the myocytes are cardiac myocytes. In some embodiments the myocytes are smooth myocytes. In other embodiments, the myocytes are combinations of skeletal, cardiac, and smooth myocytes. In some embodiments, the engineered meat comprises endothelial cells, which are microvascular endothelial cells. In some embodiments, the engineered meat disclosed herein is characterized by a ratio of non-human myocytes to non-human endothelial cells of about 19:1 to about 3:1. In some embodiments, non-human endothelial cells comprise about 5% to about 15% of the total cell population of the engineered meat. In some embodiments, the engineered meat is substantially free of non-differentiated myocytes and/or non-differentiated endothelial cells. In some embodiments, the myocytes are aligned relative to each other. In further embodiments, the myocytes are aligned relative to a layer of the meat. In various embodiments, the engineered meat disclosed herein further comprises one or more substances that enhance the nutritional value of the meat, the culinary appeal of the meat, or the growth characteristics of the non-human cells. In some embodiments, the engineered meat further comprises one or more nutritional supplements. In further embodiments, the nutritional supplements are selected from: vitamins, minerals, fiber, fatty acids, and amino acids. In some embodiments, the engineered meat further comprises one or more flavorants and/or colorants. In some embodiments, the engineered meat further comprises one or more of: matrix proteins, proteoglycans, antioxidants, perfluorocarbons, and growth factors. In some embodiments, the engineered meat is suitable for human consumption. In other embodiments, the engineered meat is suitable for non-human animal consumption. In still other embodiments, the engineered meat is suitable for both human and non-human animal consumption.

In a another aspect, disclosed herein is a plurality of multicellular bodies comprising a plurality of living non-human myocytes wherein the cells are adhered and/or cohered to one another; wherein the multicellular bodies are arranged adjacently on a support substrate to form a substantially planar layer for use in formation of engineered comestible meat. In certain embodiments, a multicellular body is substantially spherical in shape. In certain embodiments, a multicellular body is substantially cylindrical. In some embodiments, a multicellular body has a substantially circular cross section. In some embodiments, a multicellular body has an elongate shape with a square, rectangular, triangular, or other non-circular cross-sectional shape. In some embodiments, a multicellular body has a non-elongate cylindrical shape or a cuboidal shape. The term "adjacent," as used herein when referring to arrangement of multicellular bodies, means in contact and on top of, under, or next to, either horizontally or vertically relative to the support substrate.

In a another aspect, disclosed herein is a plurality of multicellular bodies comprising a plurality of living non-human myocytes wherein the cells are adhered and/or cohered to one another; wherein the multicellular bodies are arranged adjacently on a support substrate and maintained in culture to allow the multicellular bodies to fuse to form a substantially planar layer for use in formation of engineered comestible meat.

In a another aspect, disclosed herein is a plurality of multicellular bodies comprising a plurality of living non-human myocytes wherein the cells are adhered and/or cohered to one another; wherein the multicellular bodies are arranged adjacently on a support substrate and maintained in culture to allow the multicellular bodies to fuse to form a substantially planar layer for use in formation of engineered comestible meat; wherein the support substrate is permeable to fluids and nutrients and allows cell culture media to contact all surfaces of said layer. In some embodiments, the engineered layers disclosed herein further comprise non-human endothelial cells and/or non-human adipose cells. In some embodiments, the layers further comprise non-human fibroblast cells. In some embodiments, the engineered layers are characterized by a ratio of non-human myocytes to non-human endothelial cells of about 19:1 to about 3:1. In some embodiments, the non-human endothelial cells comprise about 5% to about 15% of the total cell population. In some embodiments, the engineered layers disclosed herein are characterized by a thickness adapted to allow diffusion to sufficiently support the maintenance and growth of said non-human myocytes and non-human endothelial cells in culture. In various embodiments, the engineered layers are about 100, 200, 300, 400, 500, 600, 700, 800, 900, or 1000 μm thick. In some embodiments, the thickness of the layers is about 100 μm to about 1000 μm. In further embodiments, the thickness of the layers is about 150 μm to about 900 μm. In still further embodiments, the thickness of the layers is about 200 μm to about 800 μm. In still further embodiments, the thickness of the layers is about 250 μm to about 700 μm. In still further embodiments, the thickness of the layers is about 300 μm to about 600 μm. In various embodiments, the engineered layers disclosed herein further comprise one or more substances that enhance nutritional value, culinary appeal, or growth characteristics. In some embodiments, the engineered layers further comprise one or more of: matrix proteins, proteoglycans, antioxidants, perfluorocarbons, and growth factors. In some embodiments, the plurality of multicellular bodies comprising a plurality of living non-human myocytes and non-human endothelial cells, wherein the cells are adhered and/or cohered to one another, are arranged adjacently on a support substrate to form a substantially planar layer for use in formation of engineered comestible meat and the layer is bioprinted. In some embodiments, each layer comprises multicellular bodies of about 100, 200, 300, 400, 500 μm in diameter. In some embodiments, the diameter of said multicellular bodies is about 100 μm to about 500 μm. In further embodiments, the diameter of said multicellular bodies is about 200 μm to about 400 μm. In further embodiments, the diameter of said multicellular bodies is about 200 μm to about 300 μm. In still further embodiments, the diameter of said multicellular bodies is about 250 μm to about 400 μm. In still further embodiments, the diameter of said multicellular bodies is about 300 μm to about 400 μm.

Also described herein are methods of forming a comestible engineered meat product, the method comprising: forming a plurality of planar layers, wherein each layer is formed by adjacently positioning a plurality of multicellular bodies in a plane, further wherein each multicellular body comprises a plurality of cohered non-human myocytes; culturing each of the planar layers at least until the plurality of multicellular bodies within each layer begin to fuse; stacking the plurality of layers to form a layered volume of engineered meat; and culturing the volume of meat at least until the stacks begin to fuse.

In some variations, the method may also include a step of preparing the plurality of multicellular bodies by culturing a plurality of non-human myocyte cells and non-human endothelial cells at least until the cells are cohered to one another. As mentioned above, any other appropriate non-human cell type may be included as part of some or all of the multicellular bodies forming the layers, including endothelial cells and/or adipose cells, and/or fibroblast cells.

During the formation of the engineered meat product, the layers maybe individually or collectively stacked atop other layer to create the volume of engineered meat. In some variations each successive layer is differently oriented with respect to the adjacent layer(s). For example, as they are stacked, the new layers may be rotated relative to the other layers in the volume. In some variations, each layer is rotated approximately 90° relative to the other layers as it is stacked.

In any of the engineered meat described herein the layers may be exercised as they are formed. As described in greater detail below, exercising the layers may enhance the formation of extracellular matrix (ECM). This may also orient the cells (e.g., myocytes) within a layer as it is formed. Thus, in some variations of the method of forming the engineered meat may include a step of applying mechanical, electrical or electromechanical force to exercise the myocytes in each layer.

As mentioned, any appropriate number of layers may be included. For example, the step of stacking the layers may include stacking more than about 10 layers, more than about 50 layers, more than about 100 layers, or the like.

In a another aspect, disclosed herein are methods of forming engineered meat, comprising: preparing a plurality of multicellular bodies comprising a plurality of living non-human myocytes wherein the cells are adhered and/or cohered to one another; laying more than one multicellular body adjacently onto a support substrate; allowing said multicellular bodies to fuse to form a layer; laying more than one layer adjacently onto that layer; allowing said layers to fuse to form engineered meat; and optionally, freezing said meat; provided that the engineered meat is comestible and for ingestion. In some embodiments, disclosed herein are methods of forming engineered meat, comprising: preparing a plurality of multicellular bodies comprising a plurality of non-human myocytes wherein the cells are adhered and/or cohered to one another; laying more than one multicellular body adjacently onto a support substrate; fusing said multicellular bodies to form a layer; laying more than one layer adjacently onto the first layer; and fusing said layers to form engineered meat; provided that the engineered meat is comestible. In some embodiments, the methods provided herein further comprise freezing said meat.

In a another aspect, disclosed herein are methods of forming engineered meat, comprising: preparing a plurality of elongate multicellular bodies comprising a plurality of living non-human myocytes wherein the cells are adhered and/or cohered to one another; preparing a plurality of substantially spherical multicellular bodies comprising a plurality of living non-human myocytes wherein the cells are adhered and/or cohered to one another; laying more than one elongate multicellular body and more than one substantially spherical multicellular body adjacently onto a support substrate; allowing said multicellular bodies to fuse to form a layer; laying (e.g., stacking) more than one layer adjacently onto the first layer; allowing said layers to fuse to form engineered meat; and optionally, freezing said meat; provided that the engineered meat is comestible and for ingestion. In some embodiments, disclosed herein are methods of forming engineered meat, comprising: preparing a plurality of elongate multicellular bodies comprising a plurality of non-human myocytes wherein the cells are adhered and/or cohered to one another; preparing a plurality of substantially spherical multicellular bodies comprising a plurality of non-human myocytes wherein the cells are adhered and/or cohered to one another; laying more than one elongate multicellular body and more than one substantially spherical multicellular body adjacently onto a support substrate; fusing said multicellular bodies to form a layer; laying more than one layer adjacently onto the first layer; and fusing said layers to form a volume of engineered meat; provided that the engineered meat is comestible and for ingestion. In some embodiments, the methods provided herein further comprise freezing said meat.

In some embodiments, the ratio of the elongate multicellular bodies and the substantially spherical multicellular bodies is about 0:100, 1:100, 2:100, 3:100, 4:100, 5:100, 6:100, 7:100, 8:100, 9:100, 1:10, 11:100, 12:100, 13:100, 14:100, 15:100, 16:100, 17:100, 18:100, 19:100, 1:5, 21:100, 22:100, 23:100, 24:100, 25:100, 26:100, 27:100, 28:100, 29:100, 3:10, 31:100, 32:100, 33:100, 34:100, 35:100, 36:100, 37:100, 38:100, 39:100, 2:5, 41:100, 42:100, 43:100, 44:100, 45:100, 46:100, 47:100, 48:100, 49:100, 1:2, 51:100, 52:100, 53:100, 54:100, 55:100, 56:100, 57:100, 58:100, 59:100, 3:5, 61:100, 62:100, 63:100, 64:100, 65:100, 66:100, 67:100, 68:100, 69:100, 7:10, 71:100, 72:100, 73:100, 74:100, 75:100, 76:100, 77:100, 78:100, 79:100, 4:5, 81:100, 82:100, 83:100, 84:100, 85:100, 86:100, 87:100, 88:100, 89:100, 9:10, 91:100, 92:100, 93:100, 94:100, 95:100, 96:100, 97:100, 98:100, 99:100, or 1:1. In some embodiments, the ratio of the substantially spherical multicellular bodies and the elongate multicellular bodies is about 0:100, 1:100, 2:100, 3:100, 4:100, 5:100, 6:100, 7:100, 8:100, 9:100, 1:10, 11:100, 12:100, 13:100, 14:100, 15:100, 16:100, 17:100, 18:100, 19:100, 1:5, 21:100, 22:100, 23:100, 24:100, 25:100, 26:100, 27:100, 28:100, 29:100, 3:10, 31:100, 32:100, 33:100, 34:100, 35:100, 36:100, 37:100, 38:100, 39:100, 2:5, 41:100, 42:100, 43:100, 44:100, 45:100, 46:100, 47:100, 48:100, 49:100, 1:2, 51:100, 52:100, 53:100, 54:100, 55:100, 56:100, 57:100, 58:100, 59:100, 3:5, 61:100, 62:100, 63:100, 64:100, 65:100, 66:100, 67:100, 68:100, 69:100, 7:10, 71:100, 72:100, 73:100, 74:100, 75:100, 76:100, 77:100, 78:100, 79:100, 4:5, 81:100, 82:100, 83:100, 84:100, 85:100, 86:100, 87:100, 88:100, 89:100, 9:10, 91:100, 92:100, 93:100, 94:100, 95:100, 96:100, 97:100, 98:100, 99:100, or 1:1.

In a another aspect, disclosed herein are methods of forming engineered meat, comprising: preparing a plurality of substantially spherical multicellular bodies comprising a plurality of living non-human myocytes wherein the cells are adhered and/or cohered to one another; laying more than one substantially spherical multicellular body adjacently onto a support substrate; allowing said substantially spherical multicellular bodies to fuse to form a layer; laying more than one layer adjacently onto the first layer; allowing the layers to fuse to form a volume of engineered meat; and optionally, freezing said meat; provided that the engineered meat is comestible and for ingestion. In some embodiments, disclosed herein are methods of forming engineered meat, comprising: preparing a plurality of substantially spherical multicellular bodies comprising a plurality of non-human myocytes wherein the cells are adhered and/or cohered to one another; laying more than one substantially spherical multicellular body adjacently onto a support substrate; fusing said substantially spherical multicellular bodies to form a layer; laying more than one layer adjacently onto the first layer; and fusing said layers to form a volume of engineered meat; provided that the engineered meat is comestible. In some embodiments, the methods provided herein further comprise freezing said meat.

In some embodiments, the methods of forming engineered meat disclosed herein comprise preparing a plurality of multicellular bodies comprising a plurality of living non-human myocytes wherein the cells are adhered and/or cohered to one another, wherein the multicellular bodies further comprise living, non-human adipose cells, and/or endothelial cells. In some embodiments, the multicellular bodies further comprise living, non-human fibroblast cells. In some embodiments, the methods of forming engineered meat disclosed herein comprise laying more than one multicellular body adjacently onto a support substrate, wherein the multicellular bodies are laid horizontally adjacent and/or vertically adjacent. In some embodiments, the methods of forming engineered meat disclosed herein comprise laying more than one layer adjacently onto a support substrate, wherein the layers are laid horizontally adjacent and/or vertically adjacent. In some embodiments, the support substrate is permeable to fluids and nutrients and allows cell culture media to contact all surfaces of said multicellular bodies and/or layers. In some embodiments, the methods of forming engineered meat disclosed herein comprise allowing multicellular bodies to fuse to form a layer, wherein the multicellular bodies fuse to form a layer in a cell culture environment. In some embodiments, fusing of multicellular bodies takes place over about 2 hours to about 36 hours. In some embodiments, the methods comprise allowing layers to fuse to form engineered meat, wherein the layers fuse to form engineered meat in a cell culture environment. In some embodiments, fusing of layers takes place over about 2 hours to about 36 hours. In some embodiments, the elongate multicellular bodies of non-human myocytes and non-human endothelial cells are of differing lengths. In various embodiments, the elongate multicellular bodies have a length of about 1, 2, 3, 4, 5, 6, 7, 8, 9, or 10 mm. In various embodiments, the elongate multicellular bodies have a length of about 1, 2, 3, 4, 5, 6, 7, 8, 9, or 10 cm. In some embodiments, the elongate multicellular bodies have a length ranging from about 1 mm to about 10 cm. In further embodiments, the elongate multicellular bodies have a length ranging from about 1 cm to about 8 cm. In still further embodiments, the elongate multicellular bodies have a length ranging from about 2 cm to about 6 cm. In some embodiments, the methods of forming engineered meat disclosed herein comprise laying more than one layer adjacently onto a support substrate and allowing the layers to fuse to form engineered meat. In various embodiments, the meat comprises about 10, 20, 30, 40, 50, 60, 70, 80, 90, or 100 layers. In some embodiments, the meat comprises about 10 to about 100 layers. In further embodiments, the meat comprises about 20 to about 80 layers. In still further embodiments, the meat comprises about 40 to about 60 layers. In some embodiments, the methods of forming engineered meat disclosed herein comprise preparing a plurality of multicellular bodies comprising a plurality of living non-human myocytes wherein the cells are adhered and/or cohered to one another, wherein the multicellular bodies have a diameter adapted to allow diffusion to sufficiently support the maintenance and growth of the non-human myocytes and non-human endothelial cells in culture. In various embodiments, the multicellular bodies have a diameter of about 100, 200, 300, 400, or 500 μm. In some embodiments, the multicellular bodies have a diameter of about 100 μm to about 500 μm. In further embodiments, the multicellular bodies have a diameter of about 200 μm to about 400 μm. In some embodiments, the diameter applies to multicellular bodies with substantially rod or sphere shape. In some embodiments, the methods of forming engineered meat disclosed herein comprise preparing a plurality of multicellular bodies comprising a plurality of living non-human myocytes wherein the cells are adhered and/or cohered to one another, wherein the multicellular bodies are bioprinted.

DETAILED DESCRIPTION OF THE INVENTION

Figure 1:
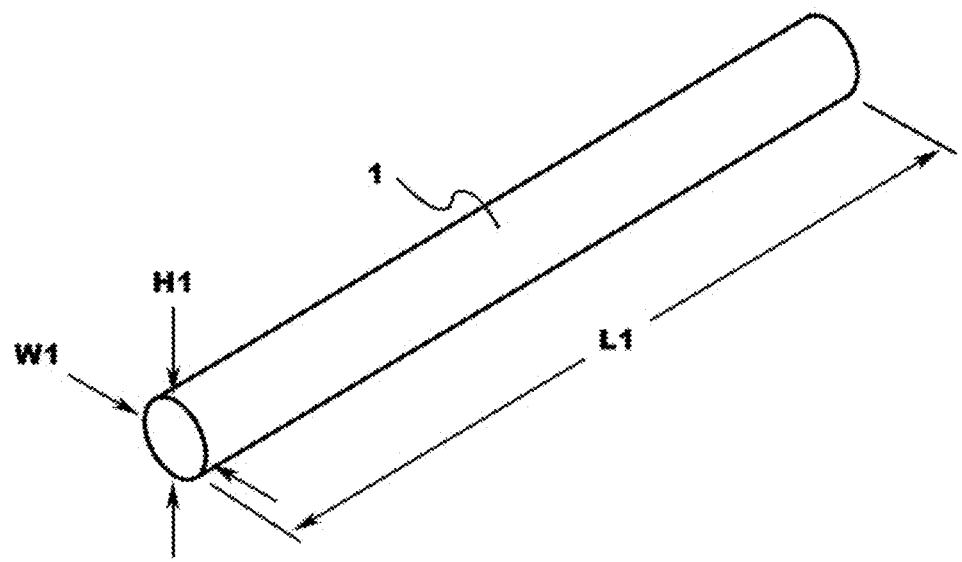
FIG. 1 depicts a non-limiting example of a multicellular body; in this case, a multicellular body 1 with width W1 that is approximately equal to height H1 and length L1 that is substantially greater than width W1 or height H1.

Tissue engineered products made using traditional materials and methods are limited in size due to the short distances gases and nutrients can diffuse to nourish interior cells. Also, existing techniques fail to provide adequate speed and throughput for mass production of engineered products. As a result, existing tissue engineering methods, used to produce meat products, result in unappealing thin sheets and pastes on a commercially infeasible scale.

Thus, an objective of the comestible meat products, layers, multicellular bodies, and methods of making the same disclosed herein is to provide commercially viable and appealing meat products. Another objective is to provide high-throughput methods that reliably, accurately, and reproducibly scale up to commercial levels. Advantages of the comestible meat products, layers, multicellular bodies, and methods of making the same disclosed herein include, but are not limited to, production of customized tissues in a reproducible, high throughput and easily scalable fashion while keeping precise control of pattern formation, particularly in cases of multiple cell types, which may result in engineered meat products with appealing flavor, texture, thickness, and appearance.

Disclosed herein, in various embodiments, is engineered meat comprising a plurality of layers, wherein each layer comprises non-human myocytes, wherein the engineered meat is comestible and for ingestion. Also disclosed herein, in various embodiments, is a plurality of multicellular bodies comprising a plurality of living non-human myocytes wherein the cells are adhered and/or cohered to one another; wherein the multicellular bodies are arranged adjacently on a support substrate to form a substantially planar layer for use in formation of engineered, comestible meat.

Also disclosed herein, in various embodiments, is a plurality of multicellular bodies comprising a plurality of living non-human myocytes wherein the cells are adhered and/or cohered to one another; wherein the multicellular bodies are arranged adjacently on a support substrate and maintained in culture to allow the multicellular bodies to fuse to form a substantially planar layer for use in formation of engineered, comestible meat.

Also disclosed herein, in various embodiments, is a plurality of multicellular bodies comprising a plurality of living non-human myocytes wherein the cells are adhered and/or cohered to one another; wherein the multicellular bodies are arranged adjacently on a support substrate and maintained in culture to allow the multicellular bodies to fuse to form a substantially planar layer for use in formation of engineered, comestible meat; wherein the support substrate is permeable to fluids and nutrients and allows cell culture media to contact all surfaces of said layer.

Also disclosed herein, in various embodiments, are methods of forming engineered meat, comprising: a) preparing a plurality of multicellular bodies comprising a plurality of living non-human myocytes wherein the cells are adhered and/or cohered to one another; b) laying more than one multicellular body adjacently onto a support substrate; c) allowing said multicellular bodies to fuse to form a layer; d) stacking more than one layer adjacently onto each other; e) allowing said layers to fuse to form engineered meat; and f) optionally, freezing said meat; provided that the engineered meat is comestible and for ingestion. Also disclosed herein, in various embodiments, are methods of forming engineered meat, comprising: a) preparing a plurality of multicellular bodies comprising a plurality of non-human myocytes wherein the cells are adhered and/or cohered to one another; b) laying more than one multicellular body adjacently onto a support substrate; c) fusing said multicellular bodies to form a layer; d) laying more than one layer adjacently onto the first layer; and e) fusing said layers to form engineered meat; wherein the engineered meat is comestible. In some embodiments, the methods further comprise freezing said meat.

Also disclosed herein, in various embodiments, are methods of forming engineered meat, comprising: a) preparing a plurality of elongate multicellular bodies and/or a plurality of substantially spherical multicellular bodies comprising a plurality of living non-human myocytes wherein the cells are adhered and/or cohered to one another; b) laying more than one elongate multicellular body and more than one substantially spherical multicellular body adjacently onto a support substrate; c) allowing said multicellular bodies to fuse to form a layer; d) stacking more than one layer adjacently onto each other on a support substrate; e) allowing said layers to fuse to form engineered meat; and f) optionally, freezing said meat; provided that the engineered meat is comestible and for ingestion. Also disclosed herein, in various embodiments, are methods of forming engineered meat, comprising: a) preparing a plurality of elongate multicellular bodies and/or a plurality of substantially spherical multicellular bodies comprising a plurality of non-human myocytes wherein the cells are adhered and/or cohered to one another; b) laying more than one elongate multicellular body and more than one substantially spherical multicellular body adjacently onto a support substrate; c) fusing said multicellular bodies to form a layer; d) stacking more than one layer adjacently onto each other on a support substrate; and e) fusing said layers to form a volume of engineered meat; provided that the engineered meat is comestible. In some embodiments, the methods comprise laying more than one elongate multicellular body and more than one substantially spherical multicellular body in different ratios adjacently onto a support substrate. In some embodiments, the methods further comprise freezing said meat.

Also disclosed herein, in various embodiments, are methods of forming engineered meat, comprising: a) preparing a plurality of substantially spherical multicellular bodies comprising a plurality of living non-human myocytes wherein the cells are adhered and/or cohered to one another; b) laying more than one substantially spherical multicellular body adjacently onto a support substrate; c) allowing said substantially spherical multicellular bodies to fuse to form a layer; d) laying more than one layer adjacently onto each other on a support substrate; e) allowing said layers to fuse to form engineered meat; and f) optionally, freezing said meat; provided that the engineered meat is comestible and for ingestion. Also disclosed herein, in various embodiments, are methods of forming engineered meat, comprising: a) preparing a plurality of substantially spherical multicellular bodies comprising a plurality of non-human myocytes wherein the cells are adhered and/or cohered to one another; b) laying more than one substantially spherical multicellular body adjacently onto a support substrate; c) fusing said substantially spherical multicellular bodies to form a layer; d) stacking more than one layer adjacently onto each other on a support substrate; and e) fusing said layers to form engineered meat; provided that the engineered meat is comestible and for ingestion. In some embodiments, the methods further comprise freezing said meat.

A basic idea underlying classical tissue engineering is to seed living cells into biocompatible and eventually biodegradable scaffold, and then culture the system in a bioreactor so that the initial cell population can expand into a tissue. Classical tissue engineering harbors several shortcomings, especially when applied to the production of meat products. First, the process of seeding cells generally involves contacting a solution of cells with a scaffold such that the cells are trapped within pores, fibers, or other microstructure of the scaffold. This process is substantially random with regard to the placement of cells within the scaffold and the placement of cells relative to each other. Therefore, seeded scaffolds are not immediately useful for production of three-dimensional constructs that exhibit planned or predetermined placement or patterns of cells or cell aggregates. Second, selection of the ideal biomaterial scaffold for a given cell type is problematic and often accomplished by trial and error. Even if the right biomaterial is available, a scaffold can interfere with achieving high cell density. Moreover, scaffold-based tissue engineering does not easily or reliably scale up to industrial levels.

In some embodiments, the engineered meat products, layers, and multicellular bodies, are made with a method that utilizes a rapid prototyping technology based on three-dimensional, automated, computer-aided deposition of multicellular bodies (e.g., cylinders and spheroids) and a biocompatible support structure (e.g., composed of agarose) by a three-dimensional delivery device (e.g., a bioprinter). The term "engineered," typically means man-made or arranged when used to refer to the layers and the meat products described herein. One example of an engineered meat may include arranging or placing multicellular bodies and/or layers to form engineered meat products by a computer-aided device (e.g., a bioprinter) according to a computer script. In further embodiments, the computer script is, for example, one or more computer programs, computer applications, or computer modules. In still further embodiments, three-dimensional tissue structures form through the post-printing fusion of the multicellular bodies similar to self-assembly phenomena in early morphogenesis.

Unlike other engineered tissues, the engineered meat described herein if formed by stacking layers of two-dimensional planar sheets of at least partially fused multicellular bodies. Thus, methods for forming even large volumes of engineered meat described herein may not require simultaneous three dimensional patterning, but may be performed by culturing (in parallel) multiple two-dimensional layers that may be later assembled into a three-dimensional assembly, or sub-assemblies that can then be stacked together. This advantageous method of forming the engineered meats described herein may permit the volume of engineered meat to be formed without requiring the need for scaffolding or three-dimensional support structures, such as filler bodies. Further, the two-dimensional layers may be formed in parallel at a relatively thin thickness that allows for diffusion of nutrients from a culture medium into the planar layer during culture (e.g., while fusing the component multicellular bodies into the layer). It is only after the component layers are stacked to form the volume that diffusion of nutrients may be limiting, resulting in cell death.

Thus, while a number of methods are available to arrange the multicellular bodies on a support substrate to produce a three-dimensional structure including manual placement, including positioning by an automated, computer-aided machine such as a bioprinter, such methods may be useful but are not required. Advantages of delivery of multicellular bodies with bioprinter technology include rapid, accurate, and reproducible placement of multicellular bodies to produce constructs exhibiting planned or pre-determined orientations or patterns of multicellular bodies and/or layers of various compositions. Advantages also include assured high cell density, while minimizing cell damage often associated with other solid freeform fabrication-based deposition methods focused on printing cells in combination with hydrogels.

The embodiments disclosed herein include methods of manufacture or making of engineered meats, and may also include business methods. In some embodiments, the speed and scalability of the techniques and methods disclosed herein are utilized to design, build, and operate industrial and/or commercial facilities for the production of comestible, engineered meat products. In further embodiments, the engineered meat products are produced, packaged, frozen, stored, distributed, marketed, advertised, and sold as, for example, food products for human beings, components or ingredients of food products for human beings, food products for non-human animals, or components or ingredients of food products for non-human animals.

Cells

Many self-adhering cell types may be used to form the multicellular bodies, layers, and engineered meat products described herein. In some embodiments, the engineered meat products are designed to resemble traditional meat products and the cell types are chosen to approximate those found in traditional meat products. In further embodiments, the engineered meat products, layers, and multicellular bodies include non-human myocytes. In still further embodiments, the engineered meat products, layers, and multicellular bodies include non-human myocytes, and/or endothelial cells, and/or adipose cells, and/or fibroblasts.

In general, the engineered meats described herein may differ from natural meats and other engineered meats by lacking blood vessels, and also lacking in nerve enervation. Even in variations in which endothelial cells are included as a component of one or more multicellular body, the engineered meat will not include blood vessels competent to transmit blood. Thus, even the large volumes of engineered meat formed by the methods described herein may not have any blood vessels. Further, the engineered meats described herein may lack any nerve components (e.g., axons, dendrites, nerve cell bodies), as they may be gown without such components.

Human beings traditionally eat several types of animal muscle tissue. Therefore, in some embodiments, the myocytes are skeletal myocytes. In some embodiments, the myocytes are cardiac myocytes. In some embodiments, the myocytes are smooth myocytes. In some embodiments, the endothelial cells are microvascular endothelial cells.

In other embodiments, the engineered meat products include neural cells, connective tissue (including bone, cartilage, cells differentiating into bone forming cells and chondrocytes, and lymph tissues), epithelial cells (including endothelial cells that form linings in cavities and vessels or channels, exocrine secretory epithelial cells, epithelial absorptive cells, keratinizing epithelial cells, and extracellular matrix secretion cells), and undifferentiated cells (such as embryonic cells, stem cells, and other precursor cells), among others.

In some embodiments, the cells used to form a multicellular body are obtained from a live animal and cultured as a primary cell line. For example, in further embodiments, the cells are obtained by biopsy and cultured ex vivo. In other embodiments, the cells are obtained from commercial sources.

The engineered meat products and the layers comprising a plurality of multicellular bodies for use in production of said meat disclosed herein are comestible and intended for consumption by human beings, non-human animals, or both. In some embodiments, the engineered meat products are human food products. In other embodiments, the engineered meat products are animal feed such as feed for livestock, feed for aquaculture, or feed for domestic pets. Therefore, in light of the disclosure provided herein, those of skill in the art will recognize that non-human cells from a plethora of sources are suitable for use in production of such products and with the methods disclosed herein. In various embodiments, the multicellular bodies, layers comprising multicellular bodies, and engineered meat products comprise non-human cells derived from, by way of non-limiting examples, mammals, birds, reptiles, fish, crustaceans, mollusks, cephalopods, insects, non-arthropod invertebrates, and combinations thereof.

In some embodiments, suitable cells are derived from mammals such as antelope, bear, beaver, bison, boar, camel, caribou, cattle, deer, elephant, elk, fox, giraffe, goat, hare, horse, ibex, kangaroo, lion, llama, moose, peccary, pig, rabbit, seal, sheep, squirrel, tiger, whale, yak, and zebra, or combinations thereof. In some embodiments, suitable cells are derived from birds such as chicken, duck, emu, goose, grouse, ostrich, pheasant, pigeon, quail, and turkey, or combinations thereof. In some embodiments, suitable cells are derived from reptiles such as turtle, snake, crocodile, and alligator, or combinations thereof. In some embodiments, suitable cells are derived from fish such as anchovy, bass, catfish, carp, cod, eel, flounder, fugu, grouper, haddock, halibut, herring, mackerel, mahi mahi, marlin, orange roughy, perch, pike, pollock, salmon, sardine, shark, snapper, sole, swordfish, tilapia, trout, tuna, and walleye, or combinations thereof. In some embodiments, suitable cells are derived from crustaceans such as crab, crayfish, lobster, prawn, and shrimp, or combinations thereof. In some embodiments, suitable cells are derived from mollusks such as abalone, clam, conch, mussel, oyster, scallop, and snail, or combinations thereof. In some embodiments, suitable cells are derived from cephalopods such as cuttlefish, octopus, and squid, or combinations thereof. In some embodiments, suitable cells are derived from insects such as ants, bees, beetles, butterflies, cockroaches, crickets, damselflies, dragonflies, earwigs, fleas, flies, grasshoppers, mantids, mayflies, moths, silverfish, termites, wasps, or combinations thereof. In some embodiments, suitable cells are derived from non-arthropod invertebrates (e.g., worms) such as flatworms, tapeworms, flukes, threadworms, roundworms, hookworms, segmented worms (e.g., earthworms, bristle worms, etc.), or combinations thereof.

Multicellular Bodies

Disclosed herein are multicellular bodies including a plurality of living non-human cells wherein the cells are adhered and/or cohered to one another. Also disclosed herein are methods comprising: preparing a plurality of multicellular bodies comprising a plurality of living non-human myocytes wherein the cells are adhered and/or cohered to one another; laying more than one multicellular body adjacently onto a support substrate; and allowing the multicellular bodies to fuse to form a substantially planar layer for used in forming engineered meat. In some embodiments, a multicellular body comprises a plurality of cells adhered and/or cohered together in a desired three-dimensional shape with viscoelastic consistency and sufficient integrity for easy manipulation and handling during a bioengineering process, such as tissue engineering. In some embodiments, sufficient integrity means that the multicellular body, during the subsequent handling, is capable of retaining its physical shape, which is not rigid, but has a viscoelastic consistency, and maintaining the vitality of the cells.

In some embodiments, a multicellular body is homocellular. In other embodiments, a multicellular body is heterocellular. In homocellular multicellular bodies, the plurality of living cells includes a plurality of living cells of a single cell type. Substantially all of the living cells in a homocellular multicellular body are substantially cells of the single cell type. In contrast, a heterocellular multicellular body includes significant numbers of cells of more than one cell type. The living cells in a heterocellular body may remain unsorted or can "sort out" (e.g., self-assemble) during the fusion process to form a particular internal structure for the engineered tissue. The sorting of cells is consistent with the predictions of the Differential Adhesion Hypothesis (DAH). The DAH explains the liquid-like behavior of cell populations in terms of tissue surface and interfacial tensions generated by adhesive and cohesive interactions between the component cells. In general, cells can sort based on differences in the adhesive strengths of the cells. For example, cell types that sort to the interior of a heterocellular multicellular body generally have a stronger adhesion strength (and thus higher surface tension) than cells that sort to the outside of the multicellular body.

In some embodiments, the multicellular bodies disclosed herein also include one or more extracellular matrix (ECM) components or one or more derivatives of one or more ECM components in addition to the plurality of cells. For example, the multicellular bodies may contain various ECM proteins including, by way of non-limiting examples, gelatin, fibrinogen, fibrin, collagen, fibronectin, laminin, elastin, and proteoglycans. The ECM components or derivatives of ECM components can be added to a cell paste used to form a multicellular body. The ECM components or derivatives of ECM components added to a cell paste can be purified from an animal source, or produced by recombinant methods known in the art. Alternatively, the ECM components or derivatives of ECM components can be naturally secreted by the cells in the multicellular body.

In some embodiments, a multicellular body includes tissue culture medium. In further embodiments, the tissue culture medium can be any physiologically compatible medium and will typically be chosen according to the cell type(s) involved as is known in the art. In some cases, suitable tissue culture medium comprises, for example, basic nutrients such as sugars and amino acids, growth factors, antibiotics (to minimize contamination), etc.

Figure 3:
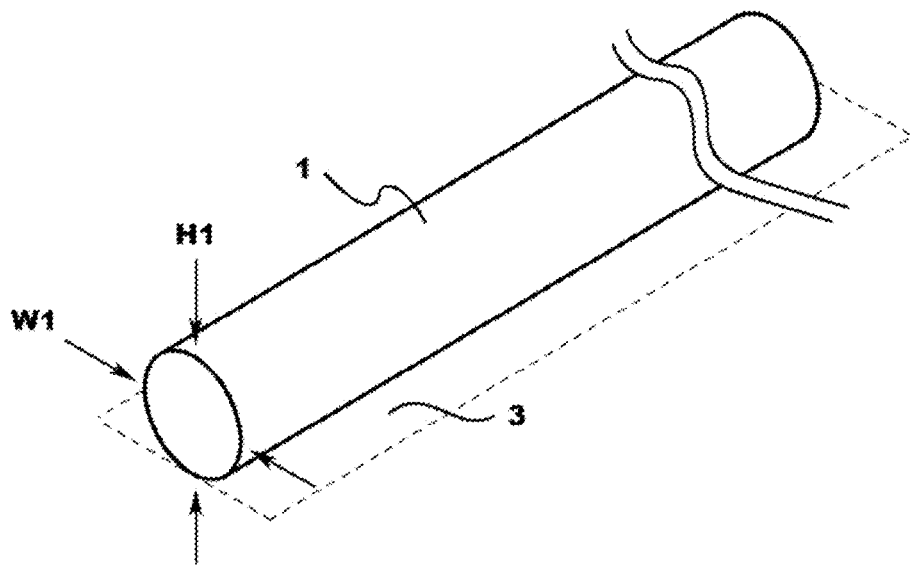
FIG. 3 depicts a non-limiting example of a multicellular body; in this case, a multicellular body 1 on a support substrate 3.
Figure 4:
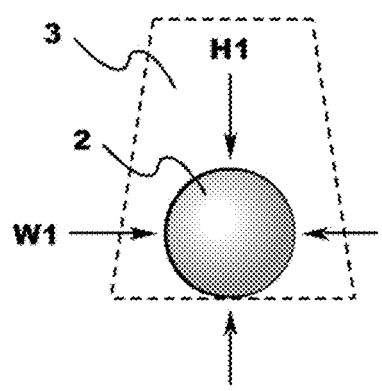
FIG. 4 depicts a non-limiting example of a substantially spherical multicellular body; in this case, a substantially spherical multicellular body 2 on a support substrate 3.

The adhesion and/or cohesion of the cells in a multicellular body is suitably sufficiently strong to allow the multicellular body to retain a three-dimensional shape while supporting itself on a flat surface. For instance, in some cases, a multicellular body supporting itself on a flat substrate may exhibit some minor deformation (e.g., where the multicellular body contacts the surface), however, the multicellular body is sufficiently cohesive to retain a height that is at least one half its width, and in some cases, about equal to the width. In some embodiments, two or more multicellular bodies placed in side-by-side adjoining relation to one another on a flat substrate form a void space under their sides and above the work surface. See, e.g., FIGS. 3 and 4. In further embodiments, the cohesion of the cells in a multicellular body is sufficiently strong to allow the multicellular body to support the weight of at least one similarly sized and shaped multicellular body when the multicellular body is assembled in a construct in which the multicellular bodies are stacked on top of one another. See, e.g., FIGS. 9 and 10. In still further embodiments, the adhesion and/or cohesion of the cells in a multicellular body is also suitably sufficiently strong to allow the multicellular body to be picked up by an implement (e.g., a capillary micropipette).

In light of the disclosure provided herein, those of skill in the art will recognize that multicellular bodies having different sizes and shapes are within the scope of the embodiments provided herein. In some embodiments, a multicellular body is substantially cylindrical and has a substantially circular cross section. For example, a multicellular body, in various embodiments, has an elongate shape (e.g., a cylindrical shape) with a square, rectangular, triangular, or other non-circular cross-sectional shape. Likewise, in various embodiments, a multicellular body has a generally spherical shape, a non-elongate cylindrical shape, or a cuboidal shape.

In various embodiments, the diameter of a multicellular body is about 50, 100, 150, 200, 250, 300, 350, 400, 450, 500, 550, 600, 650, 700, 750, 800, 850, 900, 950, 1000 µm, or quantifiable increments therein. In some embodiments, a multicellular body is configured to limit cell necrosis caused by inability of oxygen and/or nutrients to diffuse into central portions of the multicellular body. For example, a multicellular body is suitably configured such that none of the living cells therein is more than about 250 µm from an exterior surface of the multicellular body, and more suitably so none of the living cells therein is more than about 200 µm from an exterior of the multicellular body.

In some embodiments, the multicellular bodies have differing lengths. In other embodiments, multicellular bodies are of substantially similar lengths. In various embodiments, the length of a multicellular body is about 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10 mm, or quantifiable increments therein. In other various embodiments, the length of a multicellular body is about 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10 cm, or quantifiable increments therein. In some embodiments, the length of multicellular bodies is chosen to result in a shape and/or size of engineered meat product that approximates that of a traditional meat product, for example, a strip of bacon, a hamburger patty, a fish fillet, a chicken breast, or a steak.

Referring to FIG. 1, in some embodiments, a multicellular body 1 is substantially cylindrical with a width W1 roughly equal to a height H1 and has a substantially circular cross section. In further embodiments, a multicellular body 1 is elongate with a length of L1. In still further embodiments, W1 and H1 are suitably about 300 to about 600 µm and L1 is suitably about 2 cm to about 6 cm.

Figure 2:
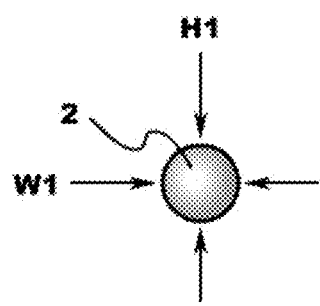
FIG. 2 depicts a non-limiting example of a substantially spherical multicellular body; in this case, a substantially spherical multicellular body 2 with width W1 that is approximately equal to height H1.

Referring to FIG. 2, in some embodiments, a multicellular body 2 is substantially spherical with a width W1 roughly equal to a height H1. In further embodiments, W1 and H1 are suitably about 300 to about 600 µm.

Layers

The engineered meat disclosed herein, includes a plurality of layers. In some embodiments, a layer includes a plurality of multicellular bodies comprising a plurality of living non-human cells wherein the cells are adhered and/or cohered to one another. Also disclosed herein are methods comprising the steps of laying multicellular bodies adjacently onto a support substrate and allowing the multicellular bodies to fuse to form a substantially planar layer for use in formation of engineered comestible meat products. In some embodiments, each layer is bioprinted, using techniques described herein.

In some embodiments, a layer includes homocellular multicellular bodies. In other embodiments, a layer includes heterocellular multicellular bodies. In yet other embodiments, a layer includes both homocellular and heterocellular multicellular bodies. In further embodiments, a layer includes non-human myocytes. In still further embodiments, a layer includes non-human myocytes, non-human endothelial cells, and adipose cells and/or fibroblast cells. In still further embodiments, a layer includes non-human myocytes, non-human endothelial cells, and other cell types disclosed herein.

In embodiments including both non-human myocytes and non-human endothelial cells, a layer may include non-human myocytes and non-human endothelial cells in a ratio of about 30:1, 29:1, 28:1, 27:1, 26:1, 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, and 1:1, or increments therein. In some embodiments, a layer contains non-human myocytes and non-human endothelial cells in a ratio of about 19:1 to about 3:1. In various embodiments, a layer includes non-human endothelial cells that comprise about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, and 25%, or increments therein, of the total cell population. In some embodiments, a layer includes non-human endothelial cells that comprise about 5% to about 15% of the total cell population. In further embodiments, the presence of endothelial cells contributes to endothelialization, described further herein.

In various embodiments, the thickness of each layer is about 10, 20, 30, 40, 50, 60, 70, 80, 90, 100, 150, 200, 250, 300, 350, 400, 450, 500, 550, 600, 650, 700, 750, 800, 850, 900, 950, 1000, 2000, 3000, 4000, or 5000 μm, or quantifiable increments therein. In some embodiments, the thickness of each layer is chosen to allow diffusion to sufficiently support the maintenance and growth of substantially all the cells in the layer in culture.

In various embodiments, the plurality of layers includes about 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, or 500 layers, or increments therein. In some embodiments, the number of layers is chosen to result in an engineered meat product with thickness that approximates that of a traditional meat product, for example, a strip of bacon, a hamburger patty, a fish fillet, a chicken breast, or a steak.

In some embodiments, the engineered layers are designed to resemble traditional meat products and design parameters (e.g., cell types, additives, size, shape, etc.) are chosen to approximate those found in traditional meat products. In further embodiments, a layer is characterized by a nutritional composition that is substantially similar to traditional meat products. In still further embodiments, a layer is characterized by a nutritional composition that is substantially 60-80 percent aqueous fluid, 14-35 percent protein, 1-25 percent fat, 1-5 percent carbohydrates and 1-5 percent other substances. In some embodiments, myocytes of the engineered layers or endothelialized meat are aligned. In some embodiments, myocytes are aligned by application of an electrical field as is known in the art. In some embodiments, myocytes are aligned by application of a mechanical stimulus, such as cyclical stretching and relaxing the substratum, as is known in the art. In further embodiments, aligned (e.g., electro-oriented and mechano-oriented) myocytes have substantially the same orientation with regard to each other as is found in many animal muscle tissues. In some embodiments, layers of multicellular bodies provided herein are exposed to electrical and/or mechanical stimulation to facilitate the formation of physiological arrangement of muscle cells.

Additives

In some embodiments, the engineered meat products, engineered layers, and/or multicellular bodies include one or more nutritional supplements. In further embodiments, one or more nutritional supplements are selected from: vitamins, minerals, fiber, fatty acids, and amino acids. In some embodiments, the engineered meat products, layers, and/or multicellular bodies include one or more additives to enhance the commercial appeal (e.g., appearance, taste, color, odor, etc.). In further embodiments, the engineered meat products, layers, and/or multicellular bodies include one or more flavorants, one or more colorants, and/or one or more odorants.

In some embodiments, the engineered meat products, engineered layers, and/or multicellular bodies include one or more of: matrix proteins, proteoglycans, antioxidants, perfluorocarbons, and growth factors. The term "growth factor," as used herein, refers to a protein, a polypeptide, or a complex of polypeptides, including cytokines, that are produced by a cell and which can affect itself and/or a variety of other neighboring or distant cells. Typically growth factors affect the growth and/or differentiation of specific types of cells, either developmentally or in response to a multitude of physiological or environmental stimuli. Some, but not all, growth factors are hormones. Exemplary growth factors are insulin, insulin-like growth factor (IGF), nerve growth factor (NGF), vascular endothelial growth factor (VEGF), keratinocyte growth factor (KGF), fibroblast growth factors (FGFs), including basic FGF (bFGF), platelet-derived growth factors (PDGFs), including PDGF-AA and PDGF-AB, hepatocyte growth factor (HGF), transforming growth factor alpha (TGF-α), transforming growth factor beta (TGF-β), including TGFβ1 and TGFβ3, epidermal growth factor (EGF), granulocyte-macrophage colony-stimulating factor (GM-CSF), granulocyte colony-stimulating factor (G-CSF), interleukin-6 (IL-6), IL-8, and the like.

In some embodiments, the engineered meat products, engineered layers, and/or multicellular bodies include one or more food preservatives known to the art. In some embodiments, the preservatives are antimicrobial preservatives including, by way of non-limiting examples, calcium propionate, sodium nitrate, sodium nitrite, sulfites (e.g., sulfur dioxide, sodium bisulfite, potassium hydrogen sulfite, etc.) and disodium ethylenediaminetetraacetic acid (EDTA). In some embodiments, the preservatives are antioxidant preservatives including, by way of non-limiting examples, butylated hydroxyanisole (BHA) and butylated hydroxytoluene (BHT).

Support Substrate

Disclosed herein, in some embodiments, is a plurality of multicellular bodies arranged adjacently on a support substrate to form a substantially planar layer for use in formation of engineered comestible meat. Also disclosed herein, in some embodiments, are methods comprising arranging multicellular bodies adjacently on a support substrate to form substantially planar layers, laying more than one layer adjacently onto a single support substrate, and allowing the layers to fuse to form engineered meat. For example, a plurality of layers may be formed as described above at the same time on different substrates then removed from their substrate when the multicellular bodies have fused sufficiently to allow them to be removed and stacked atop one another or atop a single substrate.

In general, each layer includes non-human myocytes. The cells in the central portions of such constructs are typically supplied with oxygen and nutrients by diffusion; however, gasses and nutrients typically diffuse approximately 200-300 microns into three-dimensional cellular constructs.

In some embodiments, the multicellular bodies disclosed herein have a diameter adapted to allow diffusion to sufficiently support the maintenance and growth of said non-human myocytes in culture. As a result, in further embodiments, the layers disclosed herein have a thickness adapted to allow diffusion to sufficiently support the maintenance and growth of said non-human myocytes in culture.

To facilitate and enhance diffusion, in some embodiments, a support substrate is permeable to fluids, gasses, and nutrients and allows cell culture media to contact all surfaces of multicellular bodies and/or layers during, for example, growth, maturation, and fusion. In various embodiments, a support substrate is made from natural biomaterials, synthetic biomaterials, and combinations thereof. In some embodiments, natural biomaterials include, by way of non-limiting examples, collagen, fibronectin, laminin, and other extracellular matrices. In some embodiments, synthetic biomaterials may include, by way of non-limiting examples, hydroxyapatite, alginate, agarose, polyglycolic acid, polylactic acid, and their copolymers. In some embodiments, a support substrate is solid. In some embodiments, a support substrate is semisolid. In further embodiments, a support substrate is a combination of solid and semisolid support elements.

In some embodiments, the support substrate is raised or elevated above a non-permeable surface, such as a portion of a cell culture environment (e.g., a Petri dish, a cell culture flask, etc.) or a bioreactor. In still further embodiments, an elevated support substrate further facilitates circulation of cell culture media and enhances contact with all surfaces of the multicellular bodies and/or layers.

Methods of Forming Multicellular Bodies

There are various ways to make multicellular bodies having the characteristics described herein. In some embodiments, a multicellular body can be fabricated from a cell paste containing a plurality of living cells or with a desired cell density and viscosity. In further embodiments, the cell paste can be shaped into a desired shape and a multicellular body formed through maturation (e.g., incubation). In a particular embodiment, a multicellular body is produced by shaping a cell paste including a plurality of living cells into a desired shape (e.g., a cylinder, a sphere). In further embodiments, the cell paste is incubated in a controlled environment to allow the cells to adhere and/or cohere to one another to form the multicellular body. In another particular embodiment, a multicellular body is produced by shaping a cell paste including a plurality of living cells in a device that holds the cell paste in a three-dimensional shape. In further embodiments, the cell paste is incubated in a controlled environment while it is held in the three dimensional shape for a sufficient time to produce a body that has sufficient cohesion to support itself on a flat surface, as described herein.

In various embodiments, a cell paste is provided by: (A) mixing cells or cell aggregates (of one or more cell types) and a cell culture medium (e.g., in a pre-determined ratio) to result in a cell suspension, and (B) compacting the cellular suspension to produce a cell paste with a desired cell density and viscosity. In various embodiments, compacting is achieved by a number of methods, such as by concentrating a particular cell suspension that resulted from cell culture to achieve the desired cell concentration (density), viscosity, and consistency required for the cell paste. In a particular embodiment, a relatively dilute cell suspension from cell culture is centrifuged for a determined time to achieve a cell concentration in the pellet that allows shaping in a mold. Tangential flow filtration ("TFF") is another suitable method of concentrating or compacting the cells. In some embodiments, compounds are combined with the cell suspension to lend the extrusion properties required. Suitable compounds include, by way of non-limiting examples, collagen, hydrogels, Matrigel, nanofibers, self-assembling nanofibers, gelatin, fibrinogen, etc.

In some embodiments, the cell paste is produced by mixing a plurality of living cells with a tissue culture medium, and compacting the living cells (e.g., by centrifugation). One or more ECM component (or derivative of an ECM component) is optionally included by, resuspending the cell pellet in one or more physiologically acceptable buffers containing the ECM component(s) (or derivative(s) of ECM component(s)) and the resulting cell suspension centrifuged again to form the cell paste.

In some embodiments, the cell density of the cell paste desired for further processing may vary with cell types. In further embodiments, interactions between cells determine the properties of the cell paste, and different cell types will have a different relationship between cell density and cell-cell interaction. In still further embodiments, the cells may be pre-treated to increase cellular interactions before shaping the cell paste. For example, cells may be incubated inside a centrifuge tube after centrifugation in order to enhance cell-cell interactions prior to shaping the cell paste.

In various embodiments, many methods are used to shape the cell paste. For example, in a particular embodiment, the cell paste is manually molded or pressed (e.g., after concentration/compaction) to achieve a desired shape. By way of a further example, the cell paste may be taken up (e.g., aspirated) into a preformed instrument, such as a micropipette (e.g., a capillary pipette), that shapes the cell paste to conform to an interior surface of the instrument. The cross sectional shape of the micropipette (e.g., capillary pipette) is alternatively circular, square, rectangular, triangular, or other non-circular cross-sectional shape. In some embodiments, the cell paste is shaped by depositing it into a preformed mold, such as a plastic mold, metal mold, or a gel mold. In some embodiments, centrifugal casting or continuous casting is used to shape the cell paste.

Figure 5:
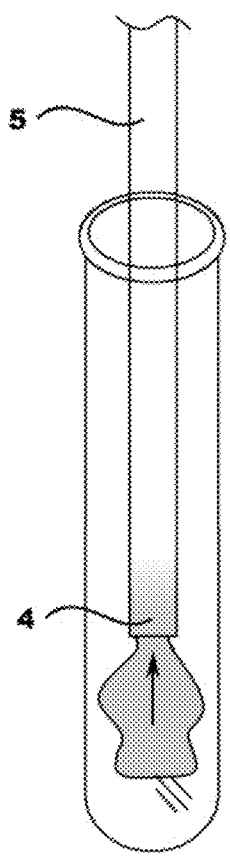
FIG. 5 depicts a non-limiting example of one method of making the multicellular bodies illustrated in FIGS. 1-4; in this case, a method involving transferring a mixed cell pellet 4 into a capillary tube 5.

Referring to FIG. 5, in a particular example, the shaping includes retaining the cell paste 4 in a shaping device 5 (e.g., a capillary pipette) to allow the cells to partially adhere and/or cohere to one another in the shaping device. By way of further example, cell paste can be aspirated into a shaping device and held in the shaping device for a maturation period (also referred to herein as an incubation period) to allow the cells to at least partially adhere and/or cohere to one another. In some embodiments, the shaping device (e.g., capillary pipette) is part of a printing head of a bioprinter or similar apparatus operable to automatically place the multicellular body in a three-dimensional construct. However, there is a limit to the amount of time cells can remain in a shaping device such as a capillary pipette, which provides the cells only limited access at best to oxygen and/or nutrients, before viability of the cells is impacted.

In some embodiments, a partially adhered and/or cohered cell paste is transferred from the shaping device (e.g., capillary pipette) to a second shaping device (e.g., a mold) that allows nutrients and/or oxygen to be supplied to the cells while they are retained in the second shaping device for an additional maturation period. One example of a suitable shaping device that allows the cells to be supplied with nutrients and oxygen is a mold for producing a plurality of multicellular bodies (e.g., substantially identical multicellular bodies). By way of further example, such a mold includes a biocompatible substrate made of a material that is resistant to migration and ingrowth of cells into the substrate and resistant to adherence of cells to the substrate. In various embodiments, the substrate can suitably be made of Teflon®, (PTFE), stainless steel, agarose, polyethylene glycol, glass, metal, plastic, or gel materials (e.g., agarose gel or other hydrogel), and similar materials. In some embodiments, the mold is also suitably configured to allow supplying tissue culture media to the cell paste (e.g., by dispensing tissue culture media onto the top of the mold).

In a particular embodiment, a plurality of elongate grooves is formed in the substrate. In a further particular embodiment, the depth of each groove is in the range of about 500 microns to about 1000 microns and the bottom of each groove has a semicircular cross-sectional shape for forming elongate cylindrical multicellular bodies that have a substantially circular cross-sectional shape. In a further particular embodiment, the width of the grooves is suitably slightly larger than the width of the multicellular body to be produced in the mold. For example, the width of the grooves is suitably in the range of about 300 microns to about 1000 microns.

Thus, in embodiments where a second shaping device is used, the partially adhered and/or cohered cell paste is transferred from the first shaping device (e.g., a capillary pipette) to the second shaping device (e.g., a mold). In further embodiments, the partially adhered and/or cohered cell paste can be transferred by the first shaping device (e.g., the capillary pipette) into the grooves of a mold. In still further embodiments, following a maturation period in which the mold is incubated along with the cell paste retained therein in a controlled environment to allow the cells in the cell paste to further adhere and/or cohere to one another to form the multicellular body, the cohesion of the cells will be sufficiently strong to allow the resulting multicellular body to be picked up with an implement (e.g., a capillary pipette). In still further embodiments, the capillary pipette is suitably be part of a printing head of a bioprinter or similar apparatus operable to automatically place the multicellular body into a three-dimensional construct.

In some embodiments, the cross-sectional shape and size of the multicellular bodies will substantially correspond to the cross-sectional shapes and sizes of the first shaping device and optionally the second shaping device used to make the multicellular bodies, and the skilled artisan will be able to select suitable shaping devices having suitable cross-sectional shapes, cross-sectional areas, diameters, and lengths suitable for creating multicellular bodies having the cross-sectional shapes, cross-sectional areas, diameters, and lengths discussed above.

As discussed herein, a large variety of cell types may be used to create the multicellular bodies of the present embodiments. Thus, one or more types of cells or cell aggregates including, for example, all of the cell types listed herein, may be employed as the starting materials to create the cell paste. For instance, cells such as non-human myocytes, endothelial cells, adipose cells, and fibroblasts are optionally employed. As described herein, a multicellular body is homocellular or heterocellular. For making homocellular multicellular bodies, the cell paste suitably is homocellular, i.e., it includes a plurality of living cells of a single cell type. For making heterocellular multicellular bodies, on the other hand, the cell paste will suitably include significant numbers of cells of more than one cell type (i.e., the cell paste will be heterocellular). As described herein, when heterocellular cell paste is used to create the multicellular bodies, the living cells may "sort out" during the maturation and cohesion process based on differences in the adhesive strengths of the cells, and may recover their physiological conformation.

In some embodiments, in addition to the plurality of living cells, one or more ECM components or one or more derivatives of one or more ECM components (e.g., gelatin, fibrinogen, collagen, fibronectin, laminin, elastin, and/or proteoglycans) can suitably be included in the cell paste to incorporate these substances into the multicellular bodies, as noted herein. In further embodiments, adding ECM components or derivatives of ECM components to the cell paste may promote cohesion of the cells in the multicellular body. For example, gelatin and/or fibrinogen are optionally added to the cell paste. More particularly, a solution of 10-30% gelatin and a solution of 10-80 mg/ml fibrinogen are optionally mixed with a plurality of living cells to form a cell suspension containing gelatin and fibrinogen.

Various methods are suitable to facilitate the further maturation process. In one embodiment, the cell paste may be incubated at about 37° C. for a time period (which may be cell-type dependent) to foster adherence and/or coherence. Alternatively or in addition, the cell paste may be held in the presence of cell culture medium containing factors and/or ions to foster adherence and/or coherence.

Arranging Multicellular Bodies on a Support Substrate to Form Layers

A number of methods are suitable to arrange multicellular bodies on a support substrate to produce a desired three-dimensional structure (e.g., a substantially planar layer). For example, in some embodiments, the multicellular bodies are manually placed in contact with one another, deposited in place by extrusion from a pipette, nozzle, or needle, or positioned in contact by an automated machine such as a bioprinter.

As described herein, in some embodiments, the support substrate is permeable to fluids, gasses, and nutrients and allows cell culture media to contact all surfaces of the multicellular bodies and/or layers during arrangement and subsequent fusion. As further described herein, in some embodiments, a support substrate is made from natural biomaterials such as collagen, fibronectin, laminin, and other extracellular matrices. In some embodiments, a support substrate is made from synthetic biomaterials such as hydroxyapatite, alginate, agarose, polyglycolic acid, polylactic acid, and their copolymers. In some embodiments, a support substrate is solid. In some embodiments, a support substrate is semisolid. In further embodiments, a support substrate is a combination of solid and semisolid support elements. In further embodiments, a support substrate is planar to facilitate production of planar layers. In some embodiments, the support substrate is raised or elevated above a non-permeable surface, such as a portion of a cell culture environment (e.g., a Petri dish, a cell culture flask, etc.) or a bioreactor. Therefore, in some embodiments, a permeable, elevated support substrate contributes to prevention of premature cell death, contributes to enhancement of cell growth, and facilitates fusion of multicellular bodies to form layers.

As described herein, in various embodiments, multicellular bodies have many shapes and sizes. In some embodiments, multicellular bodies are elongate and in the shape of a cylinder. See e.g., FIGS. 1 and 3. In some embodiments, multicellular bodies provided herein are of similar lengths and/or diameters. In other embodiments, multicellular bodies provided herein are of differing lengths and/or diameters. In some embodiments, multicellular bodies are substantially spherical. See e.g., FIGS. 2 and 4. In some embodiments, layers include substantially spherical multicellular bodies that are substantially similar in size. In other embodiments, layers include substantially spherical multicellular bodies that are of differing sizes.

Figure 6:
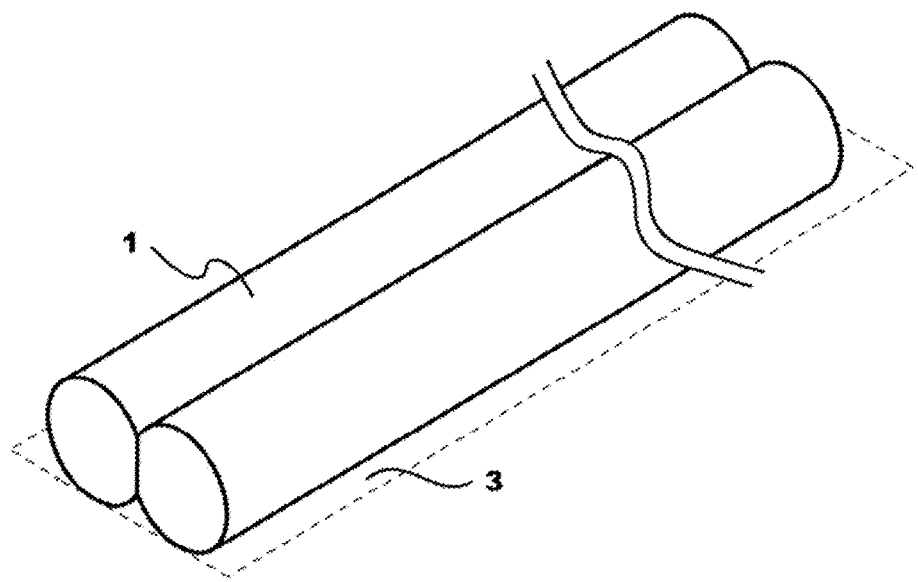
FIG. 6 depicts a non-limiting example of a plurality of multicellular bodies; in this case, a plurality of multicellular bodies 1 laid adjacently onto a support substrate 3 such that they are allowed to fuse.

Referring to FIG. 6, in some embodiments, multicellular bodies 1 are arranged on a support substrate 3 horizontally adjacent to, and in contact with, one or more other multicellular bodies to form a substantially planar layer.

Figure 7:
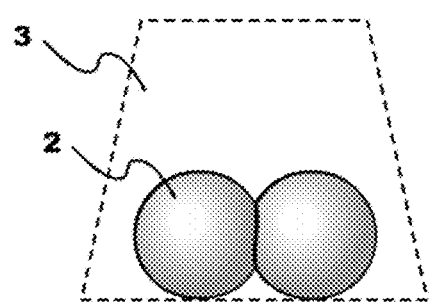
FIG. 7 depicts a non-limiting example of a plurality of substantially spherical multicellular bodies; in this case, a plurality of substantially spherical multicellular bodies 2 laid adjacently onto a support substrate 3 such that they are allowed to fuse.

Referring to FIG. 7, in some embodiments, substantially spherical multicellular bodies 2 are arranged on a support substrate 3 horizontally adjacent to, and in contact with, one or more other substantially spherical multicellular bodies. In further embodiments, this process is repeated to build up a pattern of substantially spherical multicellular bodies, such as a grid, to form a substantially planar layer.

Figure 8:
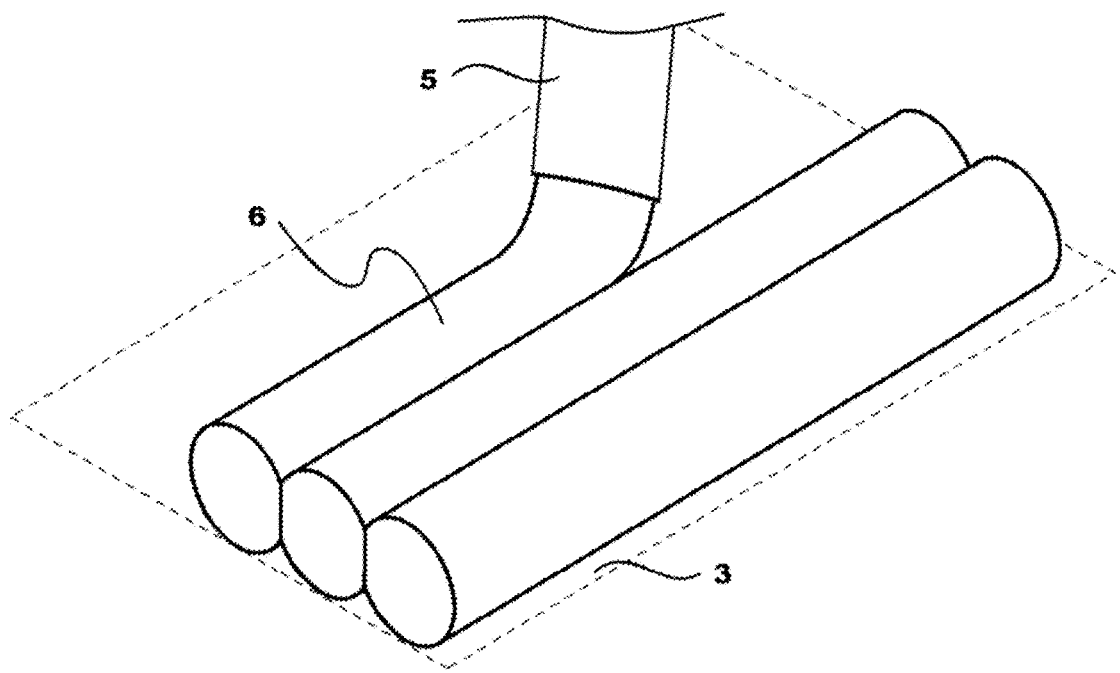
FIG. 8 depicts a non-limiting example of one method of making a layer comprising a plurality of multicellular bodies; in this case, a method involving extruding multicellular bodies 6 from a pressure-operated mechanical extruder comprising a capillary tube 5 onto a support substrate 3.

Referring to FIG. 8, in a particular embodiment, a multicellular 6 body is laid onto a support substrate 3 via an implement such as a capillary pipette 5 such that it is horizontally adjacent to, and in contact with one or more other multicellular bodies. In further embodiments, a multicellular body is laid onto a support substrate such that it is parallel with a plurality of other multicellular bodies.

Figure 9:
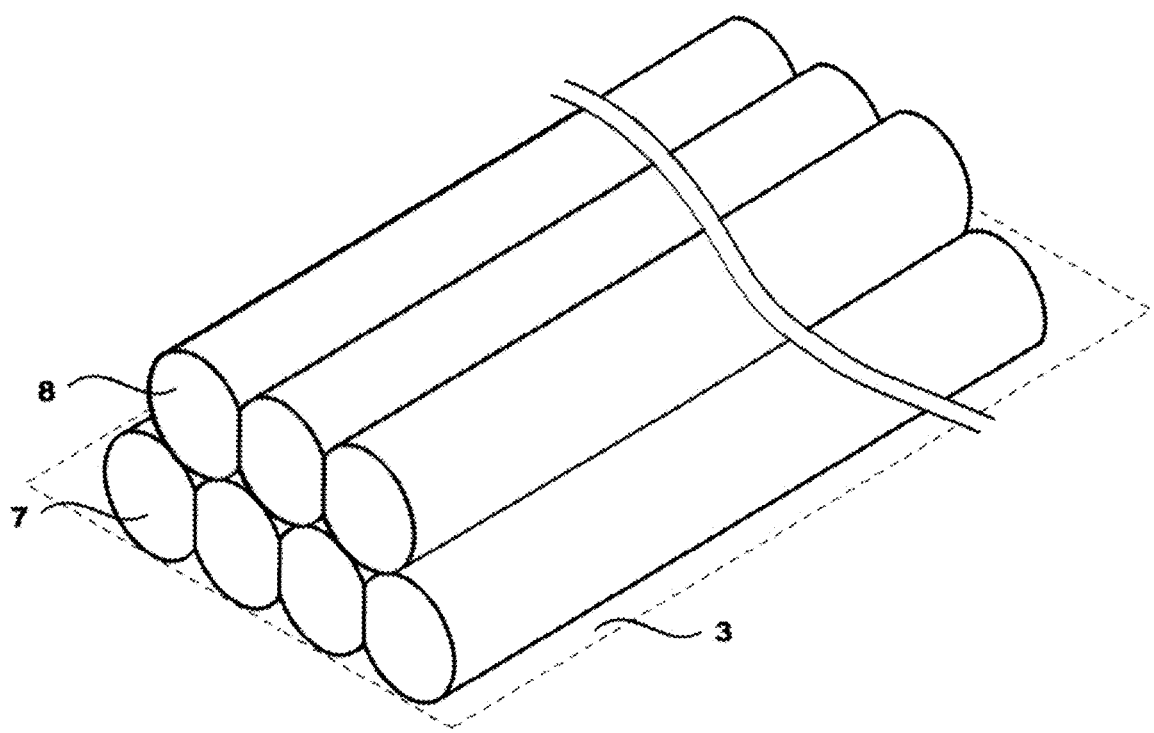
FIG. 9 depicts a non-limiting example of one method of making engineered meat; in this case, a method involving laying more than one layer, comprising a plurality of prior and subsequent multicellular bodies 7, 8, adjacently onto a support substrate 3.

Referring to FIG. 9, in some embodiments, a subsequent series of multicellular bodies 8 are arranged vertically adjacent to, and in contact with, a prior series of multicellular bodies 7 on a support substrate 3 to form a thicker layer.

In other embodiments, layers of different shapes and sizes are formed by arranging multicellular bodies of various shapes and sizes. In some embodiments, multicellular bodies of various shapes, sizes, densities, cellular compositions, and/or additive compositions are combined in a layer and contribute to, for example, appearance, taste, and texture of the resulting layer.

Figure 10:
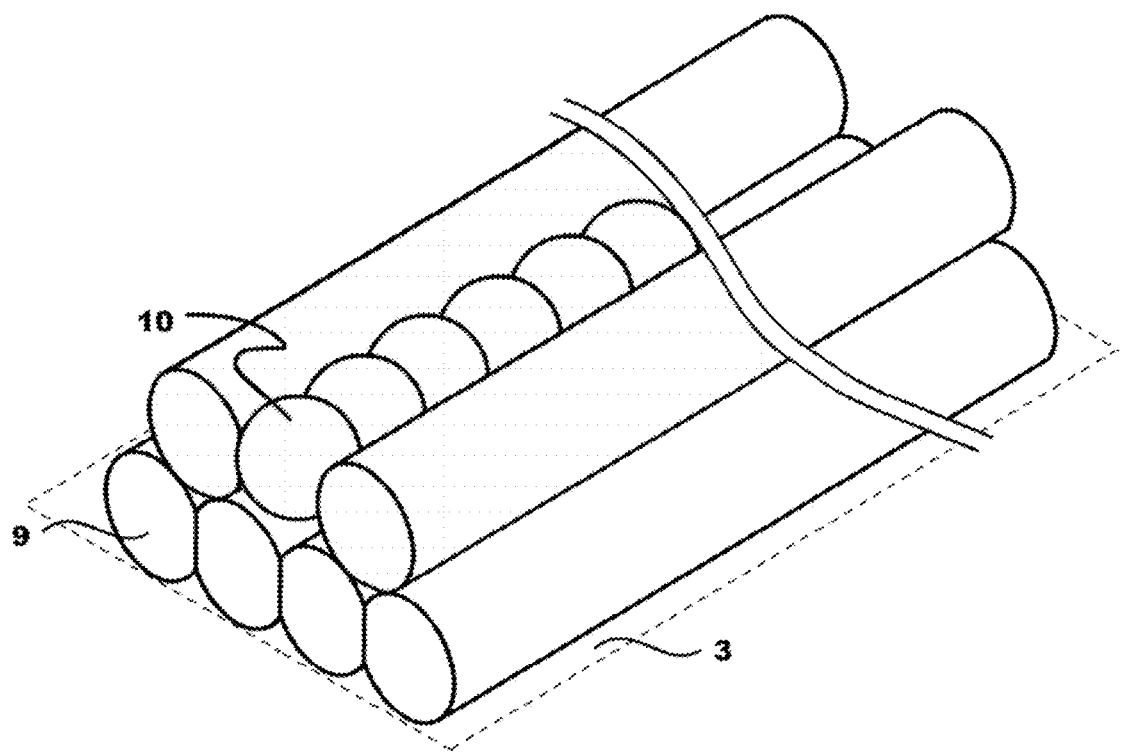
FIG. 10 depicts a non-limiting example of one method of making engineered meat; in this case, a method involving laying more than one layer, comprising a plurality of multicellular bodies 9 and a plurality of substantially spherical multicellular bodies 10, adjacently onto a support substrate 3.

Referring to FIG. 10, in some embodiments, elongate multicellular bodies 9 are arranged adjacent to, and in contact with, substantially spherical multicellular bodies 10 on a support substrate 3 to form a complex layer.

Once assembly of a layer is complete, in some embodiments, a tissue culture medium is poured over the top of the construct. In further embodiments, the tissue culture medium enters the spaces between the multicellular bodies to support the cells in the multicellular bodies. The multicellular bodies in the three-dimensional construct are allowed to fuse to one another to produce a substantially planar layer for use in formation of engineered, comestible meat. By "fuse," "fused" or "fusion," it is meant that the cells of contiguous multicellular bodies become adhered and/or cohered to one another, either directly through interactions between cell surface proteins, or indirectly through interactions of the cells with extracellular matrix (ECM) components or derivatives of ECM components. In some embodiments, the cells within the multicellular bodies produce their own cell specific ECM (e.g., collagen), which provides the mechanical integrity of the multicellular bodies and the comestible meat product. In some embodiments, a fused layer is completely fused and that multicellular bodies have become substantially contiguous. In some embodiments, a fused layer is substantially fused or partially fused and the cells of the multicellular bodies have become adhered and/or cohered to the extent necessary to allow moving and manipulating the layer intact.

In some embodiments, the multicellular bodies fuse to form a layer in a cell culture environment (e.g., a Petri dish, cell culture flask, bioreactor, etc.). In further embodiments, the multicellular bodies fuse to form a layer in an environment with conditions suitable to facilitate growth of the cell types included in the multicellular bodies. In various embodiments, fusing takes place over about 15, 20, 25, 30, 35, 40, 45, 50, 55, and 60 minutes, and increments therein. In other various embodiments, fusing takes place over about 1, 2, 3, 4, 5, 6, 7, 8, 9, 10, 11, 12, 14, 16, 18, 20, 22, 24, 26, 28, 30, 32, 34, 36, 38, 40, 42, 44, 46, and 48 hours, and increments therein. In yet other various embodiments, fusing takes place over about 1, 2, 3, 4, 5, 6, 7, 8, 9, 10, 12, and 14 days, and increments therein. In further embodiments, fusing takes place over about 2 hours to about 36 hours. Several factors influence the fusing time required including, by way of non-limiting examples, cell types, cell type ratios, culture conditions, and the presence of additives such as growth factors.

Once fusion of a layer is complete, in some embodiments, the layer and the support substrate are separated. In other embodiments, the layer and the support substrate are separated when fusion of a layer is substantially complete or partially complete, but the cells of the layer are adhered and/or cohered to one another to the extent necessary to allow moving, manipulating, and stacking the layer without breaking it apart. In further embodiments, the layer and the support substrate are separated via standard procedures for melting, dissolving, or degrading the support substrate. In still further embodiments, the support substrate is dissolved, for example, by temperature change, light, or other stimuli that do not adversely affect the layer. In a particular embodiment, the support substrate is made of a flexible material and peeled away from the layer.

In some embodiments, the separated layer is transferred to a bioreactor for further maturation. In some embodiments, the separated layer matures and further fuses after incorporation into an engineered meat product.

In other embodiments, the layer and the support substrate are not separated. In further embodiments, the support substrate degrades or biodegrades prior to packaging, freezing, sale or consumption of the assembled engineered meat product.

Arranging Layers on a Support Substrate to Form Engineered Meat

A number of methods are suitable to arrange layers on a support substrate to produce engineered meat. For example, in some embodiments, the layers are manually placed in contact with one another or deposited in place by an automated, computer-aided machine such as a bioprinter, according to a computer script. In further embodiments, substantially planar layers are stacked to form engineered meat.

In various embodiments, about 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, or 500 layers, or increments therein, are stacked. In some embodiments, about 10 to about 100 layers are stacked. In some embodiments, about 20 to about 80 layers are stacked. In some embodiments, about 40 to about 60 layers are stacked. In further embodiments, stacking is repeated to develop a thickness that approximates a traditional meat product such as a Carpaccio, a strip of bacon, a hamburger patty, a fish fillet, a chicken breast, or a steak. In various embodiments, stacked layers comprise an engineered meat product about 1, 5, 10, 15, 20, 25, 30, 35, 40, 45, or 50 mm, or increments therein, thick.

In some embodiments, a layer has an orientation defined by the placement, pattern, or orientation of multicellular bodies. In further embodiments, each layer is stacked with a particular orientation relative to the support substrate and/or one or more other layers. In various embodiments, one or more layers is stacked with an orientation that includes rotation relative to the support substrate and/or the layer below, wherein the rotation is about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, and 180 degrees, or increments therein. In other embodiments, all layers are oriented substantially similarly.

Figure 11:
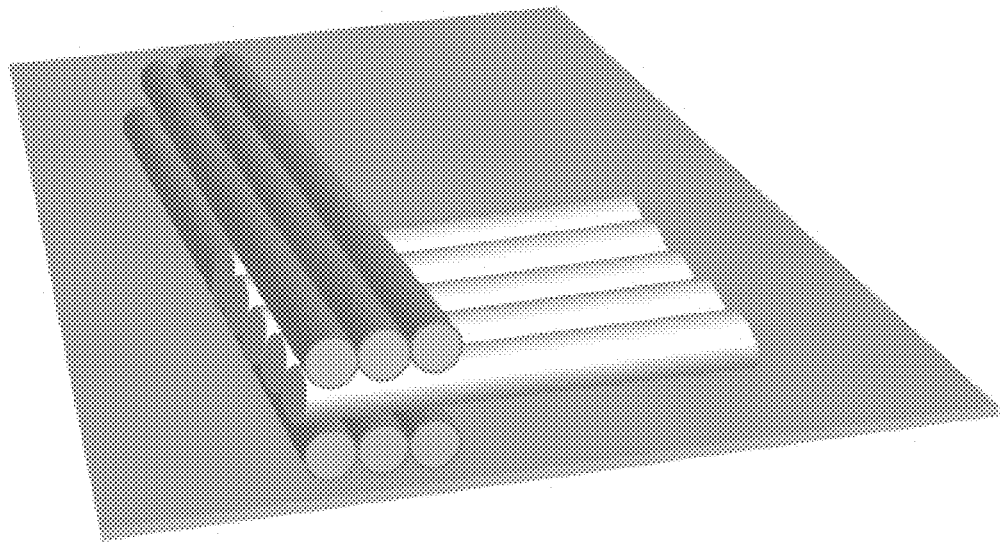
FIG. 11 depicts a non-limiting example of one method of making engineered meat; in this case, a method involving stacking more than one layer, wherein layers subsequent to the first are rotated 90 degrees with respect to the layer below.

Referring to FIG. 11, in a particular embodiment, layers have an orientation defined by the parallel placement of multicellular bodies used to form the layer. In a further particular embodiment, layers are stacked with an orientation including 90 degree rotation with respect to the layer below to form engineered meat.

Once stacking of the layers is complete, in some embodiments, the layers in the three-dimensional construct are allowed to fuse to one another to produce engineered meat. In some embodiments, the layers fuse to form engineered meat in a cell culture environment (e.g., a Petri dish, cell culture flask, bioreactor, etc.). In various embodiments, fusing takes place over about 15, 20, 25, 30, 35, 40, 45, 50, 55, and 60 minutes, and increments therein. In other various embodiments, fusing takes place over about 1, 2, 3, 4, 5, 6, 7, 8, 9, 10, 11, 12, 14, 16, 18, 20, 22, 24, 26, 28, 30, 32, 34, 36, 38, 40, 42, 44, 46, and 48 hours, and increments therein. In further embodiments, fusing takes place over about 2 hours to about 36 hours.

In some embodiments, once stacked, the cells of the multicellular bodies and layers begin to die due to the inability of gases, fluids, and nutrients, to diffuse into or otherwise reach the inner portions of the construct. In further embodiments, the gradual death of the cells is similar to the natural cell death that occurs in the tissues of a postmortem organism. In some embodiments, the layers of the engineered meat construct fuse to one another simultaneously with the gradual death of the cells. In some embodiments, the multicellular bodies of the layers continue to fuse to one another simultaneously with the gradual death of the cells. In further embodiments, fusion within and between layers is complete or substantially complete prior to the death of a majority of the cells of the construct. In further embodiments, fusion within and between layers is complete or substantially complete prior to the death of all the cells of the construct.

Once assembly of the engineered meat is complete, in some embodiments, the meat and the support substrate are separated. In further embodiments, the meat and the support substrate are separated via standard procedures for melting, dissolving, or degrading the support substrate. In still further embodiments, the support substrate is dissolved, for example, by temperature change, light, or other stimuli that do not adversely affect the meat. In a particular embodiment, the support substrate is made of a flexible material and peeled away from the meat. In some embodiments, the separated meat is transferred to a bioreactor for further maturation. In other embodiments, the meat and the support substrate are not separated. In further embodiments, the support substrate degrades or biodegrades prior to sale or consumption.

In some embodiments, the meat is irradiated. In some embodiments, the meat is frozen to prevent decomposition or degradation prior to distribution, sale, and consumption. In further embodiments, frozen meat is vacuum-packed.

Engineered Meat

Disclosed herein, in some embodiments, are engineered meat products. Also disclosed herein, in various embodiments, is a plurality of multicellular bodies arranged adjacently on a support substrate to form a substantially planar layer for use in formation of engineered meat.

In some embodiments, the engineered meat products are fresh. In other embodiments, the engineered meat products are preserved. In further embodiments, the meat is preserved by, for example, cooking, drying, smoking, canning, pickling, salt-curing, or freezing.

In some embodiments, the engineered meat products are substantially-free of pathogenic microorganisms. In further embodiments, controlled and substantially sterile methods of cell preparation, cell culture, multicellular body preparation, layer preparation, and engineered meat preparation result in a product substantially-free of pathogenic microorganisms. In further embodiments, an additional advantage of such a product is increased utility and safety.

In some embodiments, the engineered meat products are shaped. In further embodiments, the meat is shaped by, for example, controlling the number, size, and arrangement of the multicellular bodies and/or the layers used to construct the meat. In other embodiments, the meat is shaped by, for example, cutting, pressing, molding, or stamping. In some embodiments, the shape of a meat product is selected to resemble a traditional meat product such as a strip of bacon, a sausage link, a sausage patty, a hamburger patty, a hot dog, a fish fillet, a chicken breast, a chicken strip, a chicken nugget, a meatloaf, or a steak. In other embodiments, the engineered meat products are ground.

EXAMPLES

The following illustrative examples are representative of embodiments described herein and are not meant to be limiting in any way.

Example 1

Preparation of Support Substrate

To prepare a 2% agarose solution, 2 g of Ultrapure Low Melting Point (LMP) agarose was dissolved in 100 mL of ultrapure water/buffer solution (1:1, v/v). The buffer solution is optionally PBS (Dulbecco's phosphate buffered saline 1×) or HBSS (Hanks' balanced salt solution 1×). The agarose solution was placed in a beaker containing warm water (over 80° C.) and held on the hot plate until the agarose dissolves completely. The agarose solution remains liquid as long as the temperature is above 36° C. Below 36° C., a phase transition occurs, the viscosity increases, and finally the agarose forms a gel.

To prepare agarose support substrate, 10 mL of liquid 2% agarose (temperature >40° C.) was deposited in a 10 cm diameter Petri dish and evenly spread to form a uniform layer. Agarose was allowed for form a gel at 4° C. in a refrigerator.

Example 2

Culture of Porcine Aortic Smooth Muscle Cells

Freshly isolated porcine aortic smooth muscle cells (PASMCs) were grown in low glucose DMEM with 10% fetal bovine serum (Hyclone Laboratories, Utah), 10% porcine serum (Invitrogen), L-ascorbic acid, copper sulfate, HEPES, L-proline, L-alanine, L-glycine, and Penicillin G (all aforementioned supplements were purchased from Sigma, St. Louis, Mo.). Cell lines were cultured on 0.5% gelatin (porcine skin gelatin; Sigma) coated dishes (Techno Plastic Products, St. Louis, Mo.) and were maintained at 37° C. in a humidified atmosphere containing 5% $CO_2$. The PASMCs were subcultured up to passage 7 before being used to form multicellular bodies.

Example 3

Preparation of Multicellular Spheroids and Cylinders

Cell cultures were washed twice with phosphate buffered saline solution (PBS, Invitrogen) and treated for 10 min with 0.1% Trypsin (Invitrogen) and centrifuged at 1500 RPM for 5 min. Cells were resuspended in 4 mL of cell-type specific medium and incubated in 10-mL tissue culture flasks (Bellco Glass, Vineland, N.J.) at 37° C. with 5% $CO_2$ on gyratory shaker (New Brunswick Scientific, Edison, N.J.) for one hour, for adhesion recovery and centrifuged at 3500 RPM. The resulting pellets were transferred into capillary micropipettes of 300 µm (Sutter Instrument, Calif.) or 500 µm (Drummond Scientific Company, Broomall, Pa.) diameters and incubated at 37° C. with 5% $CO_2$ for 15 min. For spherical multicellular bodies, extruded cylinders were cut into equal fragments that were let to round up overnight on a gyratory shaker. Depending on the diameter of the micropipettes, this procedure provided regular spheroids of defined size and cell number. For cylindrical multicellular bodies, cylinders were mechanically extruded into specifically prepared non-adhesive Teflon® or agarose molds using a bioprinter. After overnight maturation in the mold, cellular cylinders were cohesive enough to be deposited.

The multicellular bodies were packaged into cartridges (micropipettes of 300-500 μm inner diameter). Cartridges were inserted into a bioprinter and delivered onto a support substrate according to a computer script that encodes the shape of the structure to be printed.

Example 4

Preparation of Engineered Meat

Cylindrical multicellular bodies are prepared as described in Example 3. The multicellular bodies are heterocellular and composed of the PASMCs of Example 2 and Porcine Coronary Artery Endothelial Cells (PCAEC, Genlantis, San Diego, Calif., Product No. PP30005). The ratio of myocytes to endothelial cells in the multicellular bodies is about 6:1. The multicellular bodies have a cross-sectional diameter of 300 μm and a length of either 2 cm, 3 cm, 4 cm, or 5 cm. Matured and multicellular bodies are packaged into cartridges (micropipettes of 300 μm inner diameter), which are then inserted into a bioprinter.

An agarose support substrate is prepared as described in Example 1. The support substrate is raised above the bottom of a large Petri dish by a fine mesh pedestal such that cell culture media may contact all surfaces of the multicellular bodies and layers deposited onto the substrate.

A bioprinter delivers the multicellular bodies onto the support substrate according to the instructions of a computer script. The script encodes placement of cylindrical multicellular bodies to form a substantially square monolayer with an average width of about 10 cm and an average length of about 10 cm. The multicellular bodies are placed parallel to one another with bodies of varying lengths placed end to end to form the encoded shape.

Culture medium is poured over the top of the layer and the construct is allowed to partially fuse over the course of about 12 hours at 37° C. in a humidified atmosphere containing 5% $CO_2$. During this time, the cells of the multicellular bodies adhere and/or cohere to the extent necessary to allow moving and manipulating the layer without breaking it apart.

The partially fused layers are peeled from the support and stacked. Sixty-five layers are stacked to form the engineered meat, which has an overall width and height of about 2 cm and a length and width of about 10 cm. Each layer is rotated 90 degrees with respect to the layer below. Once stacked, the cells start dying due to oxygen deprivation, as culture medium is not changed. Cell death starts in the stack's interior, as these are the first deprived of oxygen, and progressively reaches outer cells, as the surrounding culture medium gets gradually depleted in oxygen. Simultaneously with cell death the partially fused layers continue to fuse while they start fusing also in the vertical direction. Since the fusion process takes about 6 hours, while cell death takes about 20 hours, the postmortem construct is fully fused and assumes a shape similar to a square pork hamburger patty.

While the engineered meats and methods of making them have been described herein in some detail by way of illustration and example, such illustration and example is for purposes of clarity of understanding only. It will be readily apparent to those of ordinary skill in the art in light of the teachings herein that certain changes and modifications may be made thereto without departing from the spirit and scope of the invention.

What is claimed is:

1. An engineered meat product, the meat product comprising:
   a body having a layered volume;
   wherein the body comprises more than about 50 stacked planar layers, each layer having a thickness of about 100 μm to about 1000 μm, wherein the layers are at least partially fused and each planar layer comprises a plurality of at least partially fused multicellular bodies comprising non-human myocytes, non-human adipose cells, and non-human fibroblasts, wherein most of the non-human myocytes within a middle region of the volume have experienced cell death before the outer layers of the volume; and
   wherein the body does not include any blood vessels, and further wherein the engineered meat product is comestible and for ingestion.

2. The engineered meat product of claim 1, wherein the volume of the body is greater than 10 $cm^3$.

3. The engineered meat product of claim 1, wherein the stacked planar layers of the body are completely fused.

4. The engineered meat product of claim 1, wherein the myocytes are derived from a mammal, a bird, reptile, a fish, a crustacean, a mollusk, or a cephalopod.

5. The engineered meat product of claim 1, wherein said myocytes are skeletal myocytes.

6. The engineered meat product of claim 1, wherein said myocytes are cardiac myocytes.

7. The engineered meat product of claim 1, wherein said myocytes are smooth muscle myocytes.

8. An engineered meat product, the meat product comprising:
   a body having a layered volume;
   wherein the body comprises about 20 to about 80 stacked planar layers, each layer having a thickness of about 100 μm to about 1000 μm, wherein the layers are at least partially fused and each planar layer comprises a plurality of at least partially fused multicellular bodies comprising non-human myocytes, non-human adipose cells, and non-human fibroblasts, wherein most of the non-human myocytes within a middle region of the volume have experienced cell death before the outer layers of the volume; and
   wherein the body does not include any blood vessels, and further wherein the engineered meat product is comestible and for ingestion.

9. An engineered meat product, the meat product comprising:
   a body having a layered volume;
   wherein the volume comprises more than about 50 stacked planar layers, each layer having a thickness of about 100 μm to about 1000 μm, wherein each planar layer comprises a plurality of elongate multicellular bodies, a plurality of substantially spherical multicellular bodies, or a combination thereof that are laid adjacent to each other, and wherein the layers are at least partially fused, wherein the elongate multicellular bodies and substantially spherical multicellular bodies comprise non-human myocytes, non-human adipose cells, and non-human fibroblasts,
   wherein most of the non-human myocytes within a middle region of the volume have experienced cell death before the outer layers of the volume; and
   wherein the body does not include any blood vessels, and further wherein the engineered meat product is comestible.

10. The engineered meat product of claim 1, wherein the body comprises about 50 to about 500 stacked planar layers.

11. The engineered meat product of claim 9, wherein the body comprises about 50 to about 500 stacked planar layers.

* * * * *